United States Patent
Hohlbein et al.

(10) Patent No.: US 8,734,042 B2
(45) Date of Patent: May 27, 2014

(54) ORAL CARE IMPLEMENT WITH RAPID FLAVOR RELEASE

(75) Inventors: Douglas Hohlbein, Hopewell, NJ (US); James R. Brown, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 440 days.

(21) Appl. No.: 13/077,446

(22) Filed: Mar. 31, 2011

(65) Prior Publication Data
US 2011/0239387 A1  Oct. 6, 2011

Related U.S. Application Data

(60) Provisional application No. 61/319,692, filed on Mar. 31, 2010.

(51) Int. Cl.
*A46B 9/04* (2006.01)
*A46B 11/00* (2006.01)
*A61K 8/11* (2006.01)

(52) U.S. Cl.
CPC ..... *A46B 11/0003* (2013.01); *A46B 2200/1066* (2013.01); *A61K 8/11* (2013.01)
USPC ............ 401/133; 401/132; 401/134; 426/89; 15/167.1

(58) Field of Classification Search
USPC ........................ 401/89, 132, 133, 134; 426/89
See application file for complete search history.

(56) References Cited

U.S. PATENT DOCUMENTS

| | | |
|---|---|---|
| 792,471 A | 6/1905 | Smith |
| 846,900 A | 3/1907 | Bloom |
| 876,185 A | 1/1908 | Hillman |
| 1,214,556 A | 2/1917 | Vene et al. |
| 1,256,662 A | 2/1918 | Cleman et al. |
| 1,411,681 A | 4/1922 | Burlew |
| 1,500,722 A | 7/1924 | Roush |
| 1,575,317 A | 3/1926 | Carmichael |
| 1,602,531 A | 10/1926 | Itoh |
| 1,784,986 A | 12/1930 | Eisenberg |
| 1,796,367 A | 3/1931 | Grove |
| 1,797,946 A | 3/1931 | Emil |
| 1,811,833 A | 6/1931 | Simon |

(Continued)

FOREIGN PATENT DOCUMENTS

| | | |
|---|---|---|
| CA | 2236416 | 5/1997 |
| CH | 664271 | 2/1988 |

(Continued)

OTHER PUBLICATIONS

International Search Report, related to corresponding International Application No. PCT/US2005/016510, mailed Nov. 22, 2005.

(Continued)

*Primary Examiner* — David Walczak
*Assistant Examiner* — Joshua Wiljanen
(74) *Attorney, Agent, or Firm* — Ryan M. Flandro

(57) ABSTRACT

An oral care toothbrush includes a handle having a head at one end of the handle, the head having at least one cleaning element. The head has at least one oral care dispenser. The oral care dispenser is configured to release an oral care material within about five seconds when exposed to water at a temperature of about 35° C. to about 40° C.

29 Claims, 11 Drawing Sheets

(56) References Cited

U.S. PATENT DOCUMENTS

| | | | |
|---|---|---|---|
| RE19,006 E | 11/1933 | Graves | |
| 1,944,067 A | 1/1934 | Collins | |
| 1,950,767 A | 3/1934 | Abbott | |
| 1,968,303 A | 7/1934 | McMath | |
| D94,503 S | 2/1935 | Hadley | |
| 1,995,374 A | 3/1935 | Young | |
| 2,004,957 A * | 6/1935 | Messner | 424/455 |
| 2,077,758 A | 4/1937 | Johnson et al. | |
| D112,719 S | 12/1938 | Miller | |
| 2,233,831 A | 3/1941 | Burke | |
| 2,241,584 A | 5/1941 | Cohen | |
| 2,259,928 A | 10/1941 | Eaton | |
| 2,262,982 A | 11/1941 | Wolcott | |
| 2,307,493 A | 1/1943 | Davidson | |
| 2,386,085 A | 10/1945 | Babel | |
| D161,873 S | 2/1951 | Rosengard | |
| 2,649,959 A | 8/1953 | Hallahan | |
| 2,710,982 A | 6/1955 | Gillem | |
| 2,736,917 A | 3/1956 | Young | |
| 2,778,045 A | 1/1957 | Bly et al. | |
| 2,793,381 A | 5/1957 | McWhorter | |
| 2,813,290 A | 11/1957 | Aschenbach | |
| 3,068,571 A | 12/1962 | Thompson | |
| 3,078,856 A | 2/1963 | Bender et al. | |
| 3,103,935 A | 9/1963 | Woodrow | |
| 3,148,684 A | 9/1964 | Keeler | |
| 3,165,776 A | 1/1965 | Tuseth | |
| 3,301,267 A | 1/1967 | Gerardi et al. | |
| 3,316,580 A | 5/1967 | Tebbs | |
| 3,432,245 A | 3/1969 | Hudson | |
| 3,458,268 A | 7/1969 | Wozab et al. | |
| 3,491,396 A | 1/1970 | Granieri, Jr. et al. | |
| 3,501,243 A | 3/1970 | Heiskell et al. | |
| 3,536,410 A | 10/1970 | Wargoe | |
| 3,589,823 A | 6/1971 | Hendrickson | |
| 3,609,789 A | 10/1971 | Slater | |
| 3,698,405 A | 10/1972 | Walker | |
| 3,879,139 A | 4/1975 | Dahl et al. | |
| 3,917,420 A | 11/1975 | Watson | |
| 4,039,261 A | 8/1977 | Evans | |
| 4,194,290 A | 3/1980 | Vallhonrat | |
| 4,292,304 A | 9/1981 | Barels et al. | |
| 4,411,885 A * | 10/1983 | Barels et al. | 424/52 |
| 4,427,116 A | 1/1984 | Brown | |
| D278,863 S | 5/1985 | Bradley | |
| 4,598,437 A | 7/1986 | Ernest et al. | |
| 4,610,045 A | 9/1986 | Rauch | |
| 4,690,816 A | 9/1987 | Hata et al. | |
| 4,829,621 A | 5/1989 | Phenegar | |
| 4,864,676 A | 9/1989 | Schaiper | |
| 4,911,187 A | 3/1990 | Castillo | |
| 4,961,717 A | 10/1990 | Hickey | |
| 5,045,305 A | 9/1991 | Clarkson et al. | |
| 5,052,071 A | 10/1991 | Halm | |
| 5,061,106 A | 10/1991 | Kent | |
| 5,133,971 A | 7/1992 | Copelan et al. | |
| 5,145,668 A | 9/1992 | Chow et al. | |
| 5,184,719 A | 2/1993 | Gordon | |
| 5,213,428 A | 5/1993 | Salman | |
| 5,366,310 A | 11/1994 | Armelles Flors | |
| 5,390,984 A | 2/1995 | Boucherie et al. | |
| 5,393,796 A | 2/1995 | Halberstadt et al. | |
| 5,398,367 A | 3/1995 | Lu | |
| 5,476,333 A | 12/1995 | Matthews | |
| 5,490,530 A | 2/1996 | Snowden | |
| 5,522,109 A | 6/1996 | Chan | |
| 5,533,791 A | 7/1996 | Boucherie | |
| D378,166 S | 2/1997 | Savitt et al. | |
| 5,609,890 A | 3/1997 | Boucherie | |
| D378,711 S | 4/1997 | Occhetti | |
| 5,633,083 A | 5/1997 | Iwai et al. | |
| 5,860,183 A | 1/1999 | Kam | |
| 5,866,151 A * | 2/1999 | Holl et al. | 424/405 |
| 5,888,002 A | 3/1999 | Fenstersheib | |
| 5,915,868 A | 6/1999 | Frazell | |
| 6,004,059 A | 12/1999 | Zaccaria | |
| 6,007,795 A | 12/1999 | Masterman et al. | |
| 6,018,840 A | 2/2000 | Guay et al. | |
| 6,090,488 A | 7/2000 | Kweon | |
| 6,135,274 A | 10/2000 | James | |
| D435,347 S | 12/2000 | Rumsey, Jr. | |
| 6,158,444 A | 12/2000 | Weihrauch | |
| 6,179,503 B1 | 1/2001 | Taghavi-Khanghah | |
| 6,321,407 B1 | 11/2001 | Weihrauch | |
| 6,397,860 B1 | 6/2002 | Hill | |
| 6,401,291 B1 | 6/2002 | Lee | |
| 6,524,023 B2 | 2/2003 | Andersen | |
| 6,526,993 B1 | 3/2003 | Wagner | |
| 6,602,013 B2 | 8/2003 | Clark | |
| 6,669,929 B1 | 12/2003 | Boyd et al. | |
| D487,351 S | 3/2004 | Frazell | |
| 7,074,390 B2 * | 7/2006 | MacKinnon | 424/49 |
| D527,528 S | 9/2006 | Hohlbein | |
| D528,803 S | 9/2006 | Hohlbein | |
| D532,202 S | 11/2006 | Hohlbein | |
| D532,607 S | 11/2006 | Hohlbein | |
| 7,182,542 B2 * | 2/2007 | Hohlbein | 401/268 |
| 7,273,327 B2 * | 9/2007 | Hohlbein et al. | 401/132 |
| 7,331,731 B2 * | 2/2008 | Hohlbein et al. | 401/133 |
| 7,478,959 B2 | 1/2009 | Hohlbein | |
| 7,575,387 B2 * | 8/2009 | Atkin | 401/268 |
| 7,931,418 B1 * | 4/2011 | Atkin | 401/268 |
| 8,092,110 B2 * | 1/2012 | Russell et al. | 401/270 |
| 8,240,937 B2 * | 8/2012 | Sorrentino et al. | 401/282 |
| 8,376,643 B2 * | 2/2013 | Russell et al. | 401/194 |
| 2002/0106234 A1 | 8/2002 | Johnson | |
| 2002/0152538 A1 | 10/2002 | McDevitt et al. | |
| 2002/0175101 A1 | 11/2002 | Albert | |
| 2003/0039504 A1 | 2/2003 | Clark | |
| 2003/0100908 A1 | 5/2003 | Grumberg et al. | |
| 2003/0188761 A1 | 10/2003 | Garcia et al. | |
| 2004/0237226 A1 | 12/2004 | Hohlbein et al. | |
| 2005/0069372 A1 | 3/2005 | Hohlbein et al. | |
| 2005/0106112 A1 | 5/2005 | Boyd et al. | |
| 2006/0165473 A1 | 7/2006 | Hohlbein | |
| 2008/0014010 A1 | 1/2008 | Bartschi et al. | |
| 2008/0104786 A1 | 5/2008 | Hohlbein et al. | |
| 2008/0120798 A1 | 5/2008 | Sorrentino et al. | |
| 2009/0044356 A1 | 2/2009 | Noble et al. | |
| 2009/0208568 A1 | 8/2009 | Hannetel et al. | |
| 2009/0320226 A1 | 12/2009 | Robinson et al. | |

FOREIGN PATENT DOCUMENTS

| | | |
|---|---|---|
| CN | 2111027 | 7/1992 |
| CN | 2164720 | 5/1994 |
| CN | 2420901 | 2/2001 |
| CN | 1694636 | 11/2005 |
| DE | 594479 | 3/1934 |
| DE | 850981 | 9/1952 |
| DE | 3529953 | 3/1987 |
| DE | 3638696 | 5/1988 |
| DE | 4127429 | 2/1993 |
| DE | 4231817 | 3/1994 |
| DE | 4238421 | 5/1994 |
| DE | 19531368 | 2/1997 |
| DE | 19842984 | 8/2000 |
| DE | 19925568 | 12/2000 |
| EP | 0332026 | 9/1989 |
| EP | 0475314 | 3/1992 |
| EP | 0481926 | 4/1992 |
| EP | 0872195 | 10/1998 |
| EP | 1415572 | 5/2004 |
| EP | 1639913 | 3/2006 |
| ES | 2090287 | 10/1996 |
| FR | 2550429 | 2/1985 |
| FR | 2554331 | 5/1985 |
| FR | 2602129 | 2/1988 |
| FR | 2646068 | 10/1990 |
| FR | 2654598 | 5/1991 |
| FR | 2754436 | 4/1998 |
| FR | 2772569 | 6/1999 |
| FR | 2772571 | 6/1999 |
| FR | 2822658 | 10/2002 |

(56) References Cited

FOREIGN PATENT DOCUMENTS

| | | |
|---|---|---|
| FR | 2832632 | 5/2003 |
| GB | 228460 | 2/1925 |
| GB | 746649 | 3/1956 |
| GB | 2297489 | 8/1996 |
| GB | 2351015 | 12/2000 |
| GB | 2388529 | 11/2003 |
| GB | 2394653 | 5/2004 |
| JP | 10216158 | 8/1998 |
| JP | 2003245133 | 9/2003 |
| RU | 60848 | 8/2006 |
| SU | 1291019 | 2/1987 |
| SU | 1417859 | 8/1988 |
| WO | WO 87/00425 | 1/1987 |
| WO | WO 97/16995 | 5/1997 |
| WO | WO 98/57570 | 12/1998 |
| WO | WO 99/60886 | 12/1999 |
| WO | WO 01/26504 | 4/2001 |
| WO | WO 02/15736 | 2/2002 |
| WO | WO 02/26079 | 4/2002 |
| WO | WO 02/34083 | 5/2002 |
| WO | WO 02/058508 | 8/2002 |
| WO | WO 03/037210 | 5/2003 |
| WO | WO 2004/010821 | 2/2004 |
| WO | WO 2004/021914 | 3/2004 |
| WO | WO 2004/087089 | 10/2004 |
| WO | WO 2005/110149 | 11/2005 |
| WO | WO 2006/020700 | 2/2006 |
| WO | WO 2008/103597 | 8/2008 |
| WO | WO 2009/136911 | 11/2009 |

OTHER PUBLICATIONS

International Search Report, related to corresponding International Application No. PCT/US2006/062416, mailed Apr. 18, 2007.
International Search Report, related to corresponding International Application No. PCT/US2008/069629, mailed Mar. 26, 2009.
International Search Report, related to corresponding International Application No. PCT/US2009/030090, mailed Apr. 3, 2009.
International Search Report and Written Opinion in international Application No. PCT/US2011/0030720 mailed Jul. 6, 2011.
National Research Council (U.S.) Food Protection Committee, 1965, *Chemicals Used in Food Processing*, Washington, Publication No. 1274, pp. 63-258.

* cited by examiner

ORAL CARE IMPLEMENT WITH RAPID FLAVOR RELEASE

CROSS-REFERENCE TO RELATED APPLICATIONS

Each of the following patent applications is incorporated herein by reference in their entirety: U.S. application Ser. No. 12/018,817 filed Jan. 24, 2008 which is a continuation-in-part of U.S. application Ser. No. 11/314,716, filed Dec. 21, 2005, which is (1) a continuation-in-part of U.S. application Ser. No. 10/843,135, filed May 11, 2004, which is a continuation-in-part of International application PCT/US03/027455, filed Sep. 4, 2003, which claimed priority to U.S. Application 60/408,321, filed Sep. 5, 2002; (2) a continuation of U.S. application Ser. No. 29/231,483, filed Jun. 6, 2005, now U.S. Pat. No. D532,607, which is a continuation of U.S. patent application Ser. No. 29/213,754, filed Sep. 23, 2004, now U.S. Pat. No. D532,202, which is a continuation in part of co-pending U.S. patent application Ser. No. 10/843,135, filed May 11, 2004, which is a continuation in part of International application PCT/US03/27455, filed Sep. 4, 2003, which claims priority to U.S. Patent Application 60/408,321, filed Sep. 5, 2002; and (3) a continuation of U.S. application Ser. No. 29/231,487, filed Jun. 6, 2005, now U.S. Pat. No. D528,803, and U.S. application Ser. No. 12/147,087, filed Jun. 26, 2008 and published as U.S. 2009/0320226 A1.

This application also claims the benefit of U.S. Provisional Application No. 61/319,692, filed on Mar. 31, 2010.

FIELD OF THE INVENTION

The present application relates generally to toothbrushes, and, more particularly, to a toothbrush having an oral care material located within the head is rapidly released upon use.

BACKGROUND OF THE INVENTION

The advantages of good dental hygiene are well known. Often, however, toothbrushes are forgotten when one is traveling or away from home. Hotels, health care facilities, nursing homes, hospitals, daycare facilities, schools, airlines, etc. have a need for single use disposable or limited multiple use toothbrushes that may be economically supplied to and discarded by individuals without a toothbrush and/or a water supply. Such toothbrushes could be used in vending machines, or distributed in large quantities for simple, portable use from anywhere.

Various types of disposable, limited use, or portable toothbrushes are known in the art. For example, some toothbrush systems have attempted to meet some of these needs by providing toothpaste within the toothbrush itself, through an integrated channel, for distribution through the toothbrush and around the bristles. This approach can be less economical due to the added manufacturing costs of toothbrushes with integrated channels. In addition, the toothpaste in some of these integrated channel toothbrushes, not being properly sealed, has a tendency to become dry, hard and stale.

BRIEF SUMMARY OF THE INVENTION

The present application solves one or more of the problems of the related art by providing an oral care implement, comprising a handle and a head connected to one end of the handle. The head has at least one cleaning element. The head has at least one oral care dispenser. The oral care dispenser is configured to release an oral care material within about five seconds when exposed to water at a temperature of about 35° C. to about 40° C.

In one embodiment a waterless toothbrush is provided having a rupturable dispenser containing an oral care material and being connected in the bristle portion of the toothbrush for dispensing the oral care material to the teeth to provide teeth cleaning and breath freshening, to deliver a cleaning, polishing, whitening, between teeth cleaning, and breath freshening action in addition to enhancing the cleaning efficiency of a typical disposable or limited use toothbrush.

In one embodiment, a toothbrush may have (1) tooth surface cleaning provided by the toothbrush bristles or other cleaning elements and the oral care material in the rupturable dispenser; (2) between teeth cleaning provided by the toothpick; and (3) breath freshening provided by the oral care material in the rupturable dispenser.

In some embodiments, an oral care toothbrush may comprise a handle having an oral care head mounted to one end of the handle with an oral care accessory mounted to an opposite end of the handle. A plurality of oral care elements such as cleaning/massage elements, which could be bristles, extending outwardly from the outer surface of the head. The head may also include one or more structures for dispensing oral care material in the oral care field of the head.

In some embodiments, the oral care toothbrush may be characterized by its small size and light weight so that it is readily adaptable for travel use. The oral care toothbrush may be capable of having multiple functions by including an accessory as part of the toothbrush such as a toothpick, dental floss or tongue cleaner.

In some embodiments, the oral care toothbrush may include a toothpick formed at one end of the handle; and a head connected at another end of said handle, said head having a bristle block that includes a plurality of bristles and retains a gel capsule therein, the gel capsule containing a mouth care solution. In further embodiments, the gel capsule can be replaced by a quantity of toothpowder, toothpaste or a tooth cleaning gel dentifrice, to provide the cleaning benefits of the dentifrice within the rupturable dispenser.

In some embodiments, a subset of bristles in the toothbrush head may include retaining members that hold the capsule in place. The retaining members may extend out of the head's bristle block, and may be curved inward to hold the capsule. The retaining members may be made of the same material as the other bristles, and may be shorter and wider than the bristles to provide greater support and rigidity.

Further features and options will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only.

Among the advantages of some embodiments of the toothbrushes disclosed herein are that the size and configuration of the toothbrush allows discreet hygienic use, such as no fingers in the mouth, adapting it to be readily used in public areas. Such uses could be done without the need for a sink or fountain or other source of water.

BRIEF DESCRIPTION OF THE DRAWINGS

The features herein will become more fully understood from the detailed description given herein below and the accompanying drawings which are given by way of illustration only, and thus are not limitative of the present invention, and wherein.

DETAILED DESCRIPTION OF THE INVENTION

Figure 1:
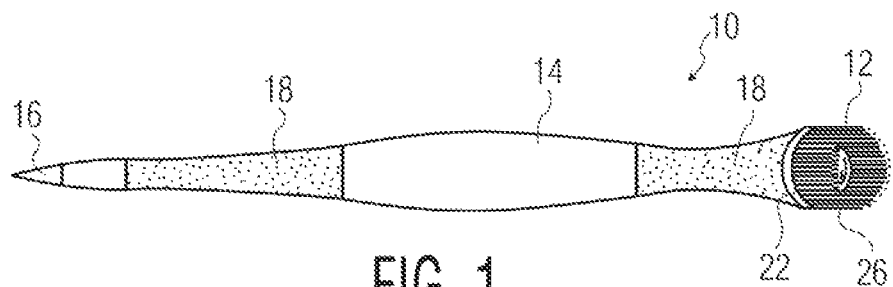
FIG. 1 is a front elevational view of an oral care toothbrush with a toothpick and a breath freshening, teeth cleaning gel capsule connected thereto.

The following detailed description refers to the accompanying drawings. The same reference numbers in different figures identify the same or similar elements.

FIGS. 1-4 illustrate an oral care toothbrush 10 that includes a head 12 and a handle 14. Head 12 may be a refill head and thus be removably connected to handle 14, or head 12 may be permanently connected to handle 14.

The majority of handle 14 and a portion of head 12 may be molded from a variety of rigid materials, including plastics, resins, etc., such as, for example, polypropylene. An end portion of the end head 12, is attached to an accessory, preferably a toothpick 16 formed of a resilient and soft thermoplastic elastomer. Toothpick 16 may be a refill and thus be removably connected to handle 14, or toothpick 16 may be permanently connected to handle 14. Toothpick 16 provides a mechanism for spot cleaning between teeth. Forming toothpick 16 of a soft elastomer provides more comfortable interproximal cleaning between teeth. Toothpick 16 could, however, be made of a stiff rigid material similar to the main portion of handle 14, or could simply be a rubber or elastomeric pick adhered or otherwise mounted to the end of handle 14.

Portions 18 of handle 14 may also be formed of a resilient and soft thermoplastic elastomer. The thermoplastic elastomer which forms toothpick 16 and handle portions 18 may be a thermoplastic vulcanate (TPV) consisting of a mixture of polypropylene and EPDM (ethylene propylene diene monomers) which is available as SANTOPRENE™ (brand), described in U.S. Pat. No. 5,393,796, or VYRAM™ (brand), another TPV consisting of a mixture of polypropylene and natural rubber. Both SANTOPRENE™ and VYRAM™ (brands) are elastomers marketed by Advanced Elastomer Systems. Other suitable elastomers include KRATON, a brand of styrene block copolymer (SBC) marketed by Shell, and DYNAFLEX G 2706 (brand), a thermoplastic elastomer marketed by GLS Corporation and which is made with KRATON (brand) polymer.

Handle 14 may further include dimples, bumps, or ridges protruding from portions of its surface, and providing a decorative appearance to handle 14 and enhanced gripping of handle 14 during use of toothbrush 10. The dimples may be formed from the same material as soft elastomer portions 18 of handle 14 or from the same material as the majority of handle 14 (e.g., a rigid material such as polypropylene). All or part of handle 14 could be made of any suitable material, such as plastic, wood, metal or various natural materials which are biodegradable. Preferably handle 14 is made of a generally flat or oval shape rather than cylindrical in its gripping portion which would be between the spaced elastomer portions 18 to facilitate the gripping of the handle.

Figure 4:
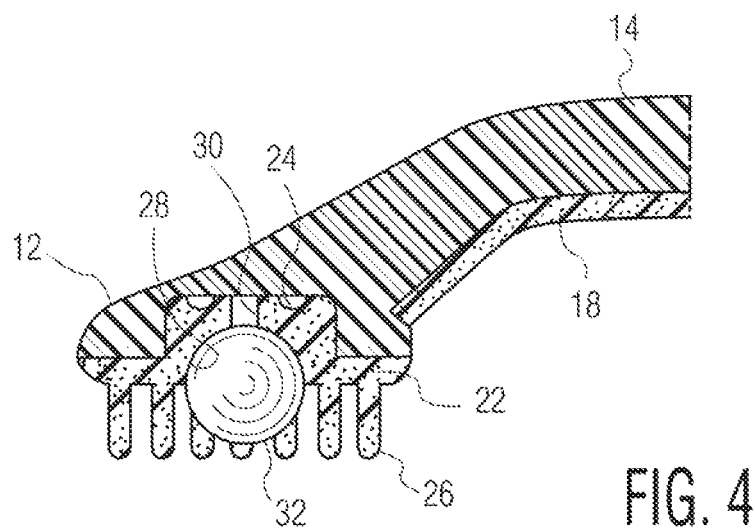
FIG. 4 is a fragmental, cross-sectional view of the head of an oral care toothbrush.

As shown in FIG. 4, another portion of head 12, defining a bristle or cleaning element block 22 of head 12, may also be formed of a resilient and soft thermoplastic elastomer, such as the thermoplastic elastomer used to form handle portions 18. Cleaning block 22 may include one or more depressions 24 provided in a surface thereof with an opening 30 therein that provides a cushioning effect to a rupturable dispenser, preferably a gel capsule 32, contained therein, as described more fully below. Cleaning block 22 further includes a multitude of cleaning elements 26 which could be conventional filament, preferably nylon, or elastomeric bristles or fingers extending integrally outwardly from the outer surface of head 12. In the illustrated embodiment as best shown in FIG. 4, all of the cleaning elements 26 extend outwardly from the outer surface of block 22 the same distance so as to create a generally flat surface. Alternatively, however, some elements 26 may be shorter or longer than other elements 26. The variable length of the cleaning elements 26 is illustrated by the dotted out tips 26a in FIG. 14, with only body portions 26b of the cleaning elements 26 shown in solid lines for purposes of clarity and to focus on the variable nature of such elements.

The term "cleaning elements" as used herein is intended to be used in a generic sense as cleaning elements or massage elements arranged in a circular cross-section shape or any type of desired shape, including straight portions or sinusoidal portions. It is to be understood that the specific illustration of the cleaning elements is merely for exemplary purposes. The features herein can, however, be practiced with various combinations of the same or different configurations (such as stapled, in-mold tufting (IMT) bristle technology as disclosed in U.S. Pat. Nos. 5,609,890, 5,390,984, and 5,533,791, the disclosures of which being incorporated by reference herein in their entirety, etc.) and/or with the same or different bristle materials (such as nylon bristles, spiral bristles, rubber bristles, etc.). Similarly, while FIGS. 1-4 illustrate the cleaning elements 26 to be generally perpendicular to the outer surface of head 12, some or all of the cleaning elements 26 may be angled at various angles with respect to the outer surface of head 12. It is thereby possible to select the combination of configurations, materials and orientations to achieve specific intended results, such as enhanced cleaning, tooth polishing, breath freshening, tooth whitening and/or massaging of the gums.

As stated above, the cleaning block 22 may include one or more depressions 24 which are designed to receive and retain an oral care dispenser, such as a rupturable gel capsule 32 therein. The one or more depressions 24 can be varied in size so as to accommodate not only varying size dispensers 32, but varying quantities of toothpowder, a toothpaste or tooth cleaning gel dentifrice or other oral care material, for delivery to the denture as the elements 26 extending from the block 22 are applied thereto, during use of the present invention such that the oral care material enhances the cleaning of the denture by the cleaning elements. While the present invention can be manufactured containing a packed toothpowder, toothpaste or tooth cleaning gel dentifrice and used repeatedly by the user refilling the dispenser with toothpowder, toothpaste or tooth cleaning gel dentifrice, it is preferably used with one or more gel capsules 32 contained therein. Most preferably the present invention is used with a single gel capsule 32, supplied therewith, so as to be most easily transported, used, and subsequently disposed of; however, it may also be used repeatedly with replaceable gel capsules 32, and then disposed of.

It is preferred that a depression in the form of a cushioned socket 28 sized and shaped receives and retains the gel capsule 32, without premature rupture of the gel capsule 32 prior to use thereof during application of the bristle block 22 to the denture and brushing thereof. Cushioning socket 28, opening 30, and the material making up bristle block 22 provide a cushioning effect for gel capsule 32 to prevent gel capsule 32 from rupturing prior to use.

Gel capsule 32 holds and applies a mouth care solution onto bristles 26 of toothbrush head 12. The mouth care solution may be toothpaste, a gel, a mouthwash, or similar dentifrice or oral hygiene product, or a combination of the same contained in the rupturable capsule 32. Preferably gel capsule 32 is a liquid-filled gel capsule having frangible, thin walls that easily rupture or burst when rubbed against the teeth, or dissolve when mixed with the saliva of a user. The materials making up gel capsule 32 and the oral or mouth care solution contained therein preferably are consumable by the user of toothbrush 10, eliminating the need for water, a sink, or a waste receptacle to expectorate the gel capsule 32 or its contents. The mouth care solution remains in gel capsule 32 until toothbrush 10 is ready for use. Gel capsule 32 may be fully sealed, helping the mouth care solution to remain fresh until use.

The capsule or dispenser 32 may include an active agent. Non-limiting examples of active agents which can be used include antibacterial agents, whitening agents, anti-sensitivity agents, anti-inflammatory agents, anti-attachment agents, plaque indicator agents, flavorants, sensates, breath freshening agents, gum health agents and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, minerals, hydrogen peroxide, urea peroxide, sodium percarbonate, PVP-H2O2, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil.

The active agent may be compatible with toothpaste, or may be unstable and/or reactive with typical toothpaste ingredients. The active agent also may be a tooth cleaning agent to boost the overall efficacy of brushing.

The active agent can be provided in any suitable vehicle, such as in aqueous solution or in the form of gel or paste. The vehicle can have a variety of different visual aesthetics including clear solution or gel or opaque solution or gel. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the active agent and the desired properties of the medium, such as viscosity.

In use, gel capsule 32 would be pressed against the teeth and burst or rupture or dissolve, applying the mouth care solution over cleaning elements 26. The user then may brush their teeth with toothbrush 10. The user may also use toothpick 16 to clean between teeth, either before or after brushing. After the user has used toothbrush 10, one may, but not necessarily, then easily and economically dispose of toothbrush 10.

The inventors have determined that in some embodiments, a user's perception of flavor intensity of the oral care material is correlated with the flavor release time of the oral care material, where the flavor release time is the amount of time between the beginning of brushing and the initial release of a first portion of the oral care material from the oral care dispenser. One suitable way in which the toothbrush and oral care industry measure flavor intensity is through a 15-point-scale having a spectrum descriptive method. During such a test, there may be a blank scale provides on a display screen with a moving cursor to mark the intensities at any given time. Appropriate software is utilized to capture the real-time intensity difference. A marked template with 0-15 point scale is used next to the blank scale on the screen. The software subsequently translates the signals numerically to 0-100. Other external scales for assessing flavor intensity exist that use reference standards. One of the widely used sets of standards in this area is from Sensory Spectrum—applicable across a wide range of products.

In some embodiments, a flavor release time of 5 seconds or less is correlated with a perception of a desired flavor intensity. The amount of oral care material initially released for this purpose can be a relatively small fraction of the total mass of oral care material. For example, in a 5 mm capsule 32 having about 55 mg of oral care material, an initial release of about 2% of the oral care material within five seconds was sufficient.

In some embodiments, an oral care implement 10 may be configured generally as shown in FIGS. 1-4, comprising a handle 14 having a head 12 at one end of the handle 14. The head 12 has at least one cleaning element 26. In some embodiments, the cleaning element comprises a plurality of cleaning bristles 26.

The head 12 has at least one oral care dispenser 32. The oral care dispenser 32 is configured to release an oral care material within five seconds when exposed to water at a temperature of about 35° C. to about 40° C. while being subjected to a pressure force. In some embodiments, the oral care dispenser 32 is configured to release the oral care material within five seconds when exposed to water or saliva at a temperature of about 37.5° C. while being subjected to the pressure force. In one embodiment, the pressure force applied to the oral care dispenser 32 is in a range of 0.68 Newtons to 0.88 Newtons, and more preferably about 0.78 Newtons.

In some embodiments, the entire structure of toothbrush 10, including head 12, handle 14, and toothpick 16, may be molded as one integral structure, using a conventional two-component injection molding operation typically used in the manufacture of toothbrushes. This enables toothbrush 10 to be economically and quickly manufactured. Although toothbrush 10 may have a variety of sizes and dimensions, it is preferred that toothbrush 10 have a small profile, with head 12 being small enough to cover one tooth at a time and handle being thinner than conventional, everyday toothbrush handles. Toothbrush 10 is thus readily portable or space saving.

The toothbrush 10 may provide many benefits, including the cosmetic benefits of brushing one's teeth in a form that can be used when one is away from home, and away from a water supply. The cosmetic benefits achieved by the toothbrush 10 include the cleaning of debris between teeth with toothpick 16, broad tooth surface cleaning (particularly the front teeth) with cleaning elements 26 and the mouth care solution of gel capsule 32, and breath freshening with the mouth care solution of gel capsule 32.

In addition to the cosmetic benefits, the toothbrush 10 may also provide economic benefits in the form of an inexpensive toothbrush that is both quickly and economically manufactured. Toothbrush 10 also provides a mechanism for maintaining oral health, without the need for toothpaste, water, mouth wash, and containers to hold the same. Thus, toothbrush 10 is also very convenient to use.

Furthermore, the toothbrush 10 provides at least one benefit of preventing the spread of waterborne diseases. For example, the toothbrush 10 eliminates the conventional practice of using local water to mix with toothpaste. This feature is useful for military applications where there is a limited source of potable water or a need to conserve water or maintain the oral health of troops, such as in desert fighting environments. In another situation, the toothbrush 10 is useful in outdoor camping environments to prevent disease or sickness from waterborne bacteria.

Although FIGS. 1-4 illustrate a manually-operated, disposable toothbrush, the features herein may also be practiced where the head includes one or more power or electrically operated movable sections carrying cleaning elements. Such movable section may oscillate in a rotational manner or may oscillate linearly in a longitudinal direction with respect to the longitudinal axis of the head or may oscillate linearly in a lateral or transverse direction with respect to the longitudinal axis of the head. The movable section may oscillate in and out in a direction toward and away from the outer surface of the head. The movable section may rock back and forth with respect to the outer surface of the head. The movable section may rotate continuously in the same direction, rather than oscillate. Any suitable drive mechanism may be used for imparting the desired motion to the movable section. Where plural movable sections are used, all of the movable sections may have the same type and direction of movement, or combinations of different movements may be used.

In some embodiments, the cleaning elements 26 may be in the form of bristles made from conventional materials, such as nylon, as well as from a combination of materials so as to provide the proper stiffness in an economical manner. For example, the cleaning elements 26 could be made of a flexible resilient material, such as TPE and a lesser expensive material such as LLDPE (linear low density polyethylene) or EVA (ethylene vinyl acetate) or a TPE. The cleaning elements could be made of a blend of TPE and either LLDPE, EVA, or polypropylene. Preferably, the two materials are combined to provide a stiffness of less than 600 MPa. The blend of materials would give the properties of conventional nylon bristles, while offering reduced costs. For example, there would be lower manufacturing costs by injection molding instead of conventional bristle tufting. Alternatively the resilient material could be a single material, such as hard TPE (i.e. Shore A 80 hardness), straight LLDPE or straight EVA.

The cleaning elements 26 may be of any desired shape. For example, the cleaning elements could be of cylindrical shape having a uniform diameter throughout their length. Alternatively, the cleaning elements 26 could taper from the root of each cleaning element where it extends from head 22 to its outer cleaning end. Since a preferred practice of the invention is to provide a small lightweight toothbrush the dimensions of the various components of toothbrush 10 are preferably small. Thus, for example, each cleaning elements may extend outwardly from the outer surface of cleaning block 12 a distance no greater than 10 mm and preferably no greater than 8 mm and most preferably no greater than 6 mm. Where tapered cleaning elements are used the root diameter should be no greater than 1.5 mm, preferably no greater than 1 mm, most preferably no greater than 0.7 mm or no greater than 0.5 mm or no greater than 0.3 mm. The diameter could then decrease in size to no greater than 0.2 mm at a distance of no greater than 6 mm from the base of the cleaning element. The taper relationship of diameter at a distance location above the root diameter could be a range of no greater than 1 mm at a distance of no greater than 10 mm, preferably no greater than 0.6 mm at a distance of no greater than 8 mm, most preferably no greater than 0.2 mm at a distance of no greater than 6 mm. Preferably, the length of the entire toothbrush 10 is no greater than 5 inches, preferably no greater than 4 inches, and more preferably no greater than 3.75 or 3 or 2.50 inches, and may be in the range of 2 to 4 inches.

Figure 14:
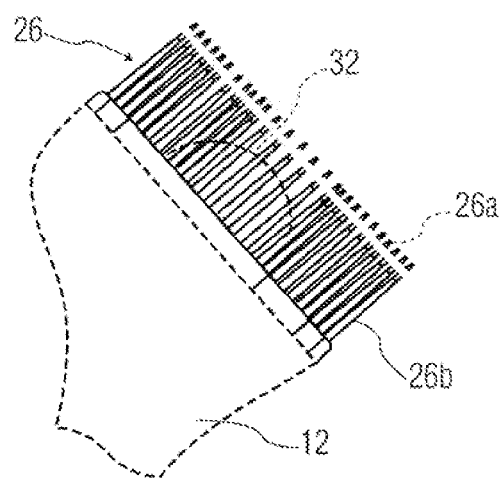
FIG. 14 is a side view of a head of an embodiment with only portions of the cleaning elements shown in solid lines for purposes of focus and clarity.

As illustrated in FIGS. 1 and 4 the cleaning elements 26 define a cleaning field in the head and the dispenser 32 is mounted within this cleaning field. The cleaning elements 26 preferably extend outwardly from the cleaning block 22 to be approximately flush with the outer surface of the gel bead or capsule 32, as shown in FIG. 4. The features herein, however, can also be practiced where the cleaning elements extend either a greater distance or a lesser distance than the dispenser 32 as shown in FIG. 14. Since toothbrush 10 is intended to be both small and lightweight, it is preferred that toothbrush 10 weigh no more than 3 grams. The small size is such that it can be held completely within the palm of an adult user. Head 12 is of a size that it would correspond to the size of an individual tooth or an individual tooth and the interproximal areas. Head 12 could be made of any suitable shape and is preferably of circular or oval shape having a maximum lateral dimension or diameter of no greater than 13 mm, preferably no greater than 12 mm and most preferably no greater than 11 mm. Where head 12 is of non-circular shape its maximum lateral dimension is 14 mm.

Figure 2:
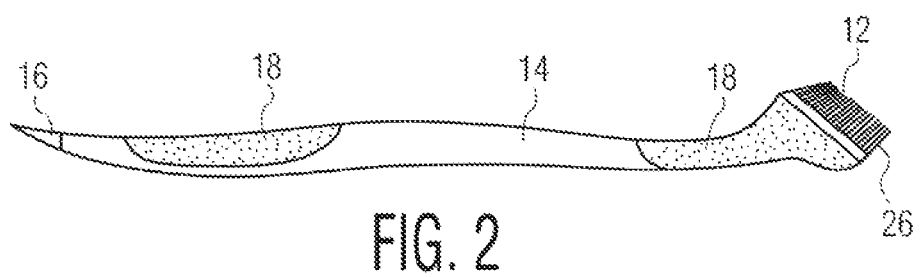
FIG. 2 is a side elevational view of the toothbrush shown in FIG. 1.

As shown in FIG. 2 head 12 may be at an angle between 0° and 90° to the longitudinal axis of handle 14. The preferred angle is from 20° to 70° and more preferably from 30° to 60°. The cleaning elements 26 could be perpendicular to the outer surface of head 12 or could also be at an angle to the outer surface such as in the range of 60° to 90° or in the range of 75° to 90°.

In one embodiment, the cleaning elements 26 could be hollow, such as hollow bristles, which are capable of absorbing a medicament by capillary action. Such a feature would be particularly useful for children where a medicament or some form of flavor could be dispensed from the hollow cleaning elements. It is also possible to leach antibacterial material from the cleaning elements. In one embodiment where the cleaning elements are used to dispense oral care materials the cleaning elements themselves may be considered as the oral care dispensers without requiring additional dispensers such as capsule 32.

Where specific parameters and characteristics have been given for cleaning elements, the features herein could be practiced where other cleaning elements do not include those parameters and characteristics.

Figure 5:
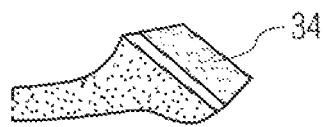
FIGS. 5-6 are side elevational views of other forms of heads for an oral care toothbrush.
Figure 6:
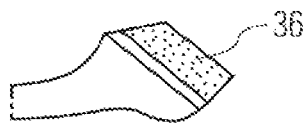

FIGS. 5-6 show other variations wherein the cleaning elements are in the form of a single mass having an irregular outer surface. As shown in FIG. 5 the mass 34 is similar to that of "steel wool" as used in household cleaning or could be part of VELCRO, formations, such as hooks or loops.

FIG. 6 shows a variation where the cleaning element 36 is of a single mass of foam for cotton which could be used as a swab for oral care material. The outer surface of the swab could be generally planar or could have surface irregularities. In such practice of the invention the oral care material could be included in the cleaning element 36 or the cleaning element 36 could be dipped into oral care material so as to absorb the material and thereby the cleaning element 36 would also function as the oral care dispenser. Such swab type cleaning elements are gentle for children, particularly infants.

Figure 7:
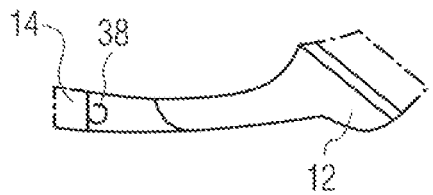
FIG. 7 is a fragmental side elevational view showing a head detachably mounted to the handle for an alternate embodiment.

The features herein could be practiced where the various components of the toothbrush 10 are segmented for manufacturing and assembly purposes. Such segmented components could also be detachably connected together so as to permit the interchangeability of the components thereby providing the possibility for the substitution of different components in the combination. Thus, the head 12 could be detachably connected to the handle 14. FIG. 7, for example, illustrates head 12 to be detachably mounted to handle 14 by a snap fitting 38 which may be of any suitable construction as is known to those of ordinary skill in the art.

The concept of a detachable interconnection may also be used wherein the dispenser 32 is detachably mounted in the head 12 or wherein the oral care accessory, such as toothpick 16, is detachably mounted to handle 14. Thus, as later described with respect to FIGS. 12 and 13 the toothbrush 10 and its various components could be packaged wherein the same package includes a plurality of toothbrushes and/or a plurality of different components such as heads, dispensers or accessories.

Figure 8:
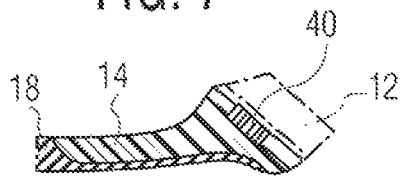
FIG. 8 is a fragmental cross-sectional elevational view showing a vibrating toothbrush head for an alternate embodiment.

FIG. 8 shows a further embodiment wherein a piezoelectric crystal 40 is provided in the handle 14 at the junction with head 12 so as to cause the head 12 to vibrate during use. Alternatively the head 12 could be mounted to a rotatable shaft extending from the handle and having an eccentric weight on the shaft to cause the head to vibrate.

Figure 3:
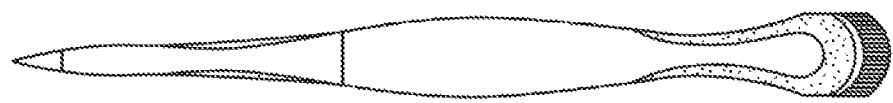
FIG. 3 is a rear elevational view of the toothbrush shown in FIGS. 1-2.
Figure 9:
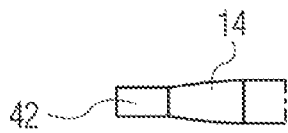
FIGS. 9-10 are fragmental front elevational views partly broken away of portions of a handle for an alternate embodiment.

Although FIGS. 1-3 illustrate an oral care accessory 16 in the form of a toothpick, other types of accessories 42 could be used as schematically shown in FIG. 9. As illustrated therein such accessory 42 would be mounted to the end of handle 14 similar to the mounting of toothpick 16. Such mounting could be detachable or of a permanent nature. Examples of such oral care accessories include tongue cleaners, floss holders or an interproximal brush. Similarly, the accessory could be of a swab or foam type similar to the cleaning element 36 of FIG. 6 or could be of the single mass of roughened material such as the cleaning element 34 of FIG. 5.

Figure 10:
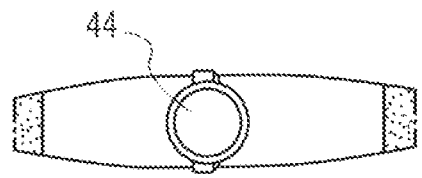

FIG. 10 shows another variation wherein the toothbrush 10 is particularly adapted for use by children. Such use is enhanced by providing any suitable ornament or caricature 44 on the toothbrush 10, such as on the handle 14 or on any other suitable location including the backside of the head 12. Such ornament 44 could be detachably mounted so that it could be kept by the child after the rest of the toothbrush 10 is thrown away. Other aspects of the invention which make it desirable for use by children include the possibilities of dispensing various types of oral care materials including materials having special flavors, tooth numbing materials, anti-sensitive materials or various medicaments.

The toothbrush 10 could also be made of various colors for different parts of the toothbrush 10. For example, soft elastomer 18 could be made of a different, such as a contrasting, color with respect to the remainder of handle 14 which would be made of a rigid material. Similarly, the head 12 could be made of a different color than the rigid portion of the handle 14 and/or the soft elastomer portions 18. The cleaning elements 26 could be made of distinct colors and the dispenser 32 could also be made of a distinct color. Along the same lines the accessory such as toothpick 16 or other accessory 42 could be made of a distinct color. These various colors could be contrasting or complementary with each other. Thus, for example, the various colors could differ only slightly in color or shade.

Figure 11:
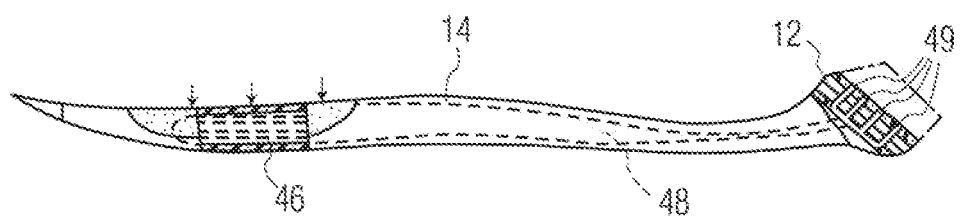
FIG. 11 is a side elevational view partly in section of yet another embodiment.

FIG. 11 illustrates another embodiment wherein the handle 14 has a hollow chamber 46 in which the oral care material could be contained. Chamber 46 leads to a passageway 48 which extends to the head 12 such as terminating in a plurality of branches 49 at the outer surface of the head 12 within the cleaning field. In order to dispense the oral care material located in the chamber or reservoir 46, handle 14 would have sufficient resiliency so that it can be squeezed thereby forcing the material from the handle 14 to the head 12 into a dispensing cavity or one or more dispensing openings.

In some embodiments, the oral care dispenser 32 comprises a hollow chamber 46 within the handle 14 containing the oral care material in a liquid form, and the oral care instrument is configured to provide a target flavor release time. To improve the flavor release time (e.g., to achieve a desired flavor release time within about five seconds), a variety of techniques may be used. For example, in some embodiments, the material of handle 14 in the vicinity of reservoir 46 is made thinner and/or softer, to facilitate rapid squeezing and ejection of the oral care material. In some embodiments, the oral care material is provided with a lower viscosity to facilitate ejection. The portion of the handle having the hollow chamber can be formed of a polyethylene, preferably a low-density polyethylene, to facilitate squeezing and ejection.

Figure 15:
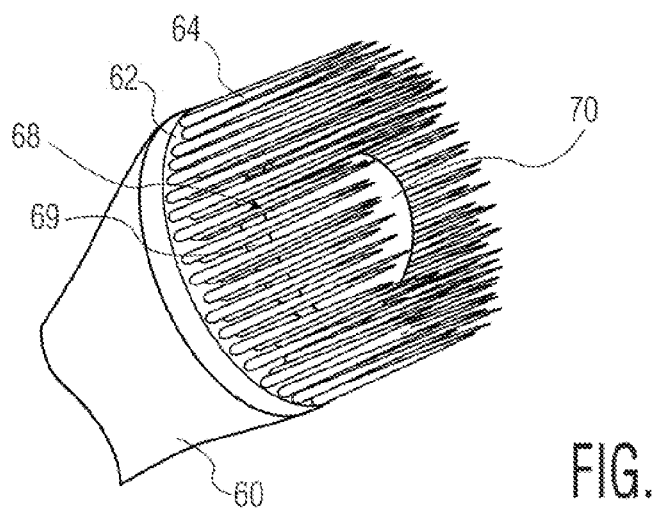
FIG. 15 is a perspective view of one embodiment of a toothbrush head.
Figure 16:
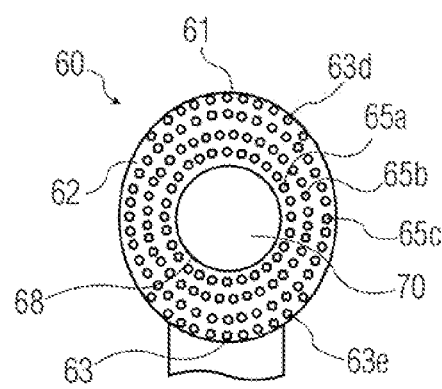
FIG. 16 is an enlarged perspective front view of the head of FIG. 15.

FIGS. 15 and 16 illustrate a head 60 according to another embodiment, the head 60 having an outer surface 62, a plurality of cleaning elements 64 extending from a portion of the outer surface 62, and a raised socket 68 extending from another portion of the outer surface 62. The socket 68 may be formed from the same material as the outer surface 62, and can be integrally formed with the outer surface such as by molding or the like. The socket 68 extends outwardly relative to the outer surface 62 by an upstanding wall 69, and includes a seat to accommodate an oral care dispenser such as a bead or capsule 70 as discussed herein. The raised socket 68 positions the dispenser 70 closer to the edges of the cleaning elements 64 to facilitate contact between the dispenser 70 and the user's teeth and to encourage rupturing of the dispenser 70 early in the brushing process. The socket 68 may also position the dispenser 70 beyond the cleaning elements 64 as discussed above, which would encourage even greater and immediate contact with the user's teeth.

The cleaning elements 64 may comprise a variety of configurations as discussed above, such as a circular configuration as shown in FIG. 1, FIG. 16 illustrates an example of an oval configuration, wherein the cleaning elements 64 are arranged in a plurality of concentric rings 65a, 65b, 65c, surrounding the socket 68. One of such rings is a partial ring comprised of partial ring sections 65d, 65e defined along the upper and lower edges 61, 63 of the outer surface 62 of the head 60, which sections 65d, 65e comprise the equivalent of a so-called power tip that is designed to provide a cleaning edge that extends beyond the majority of the field of cleaning elements for increased efficacy.

Any suitable oral care products could be dispensed from the dispenser. Such products include, but are not limited to the gel capsule 32 as previously described and could contain toothpaste, tooth powder or could be a small vial of mouthwash having a gel, a powder or a liquid. Such a vial could be separately included in a package containing the toothbrush. The materials could be flavored and could be provided in sets of different flavors and/or different characteristics such as medicaments, numbing materials, etc.

Where the dispensers 32 are in the form of beads, different beads or capsules could be used with different colors/flavors to enhance consumer appeal. As described the capsule 32 could be a liquid-filled bead that bursts. Suitable beads include those supplied by Mane Inc. of Milford, Ohio.

Any suitable methods may be used for forming toothbrush 10 and its various components. For example, multi-component injection molding could be used to integrally couple various components such as the cleaning elements 26 and the head 12 and/or the handle 14. This could be done in an automated or multiple step process. The handle could be rotocast blow molded to form a hollow squeeze handle that would be usable in the embodiment shown in FIG. 11.

Figure 12:
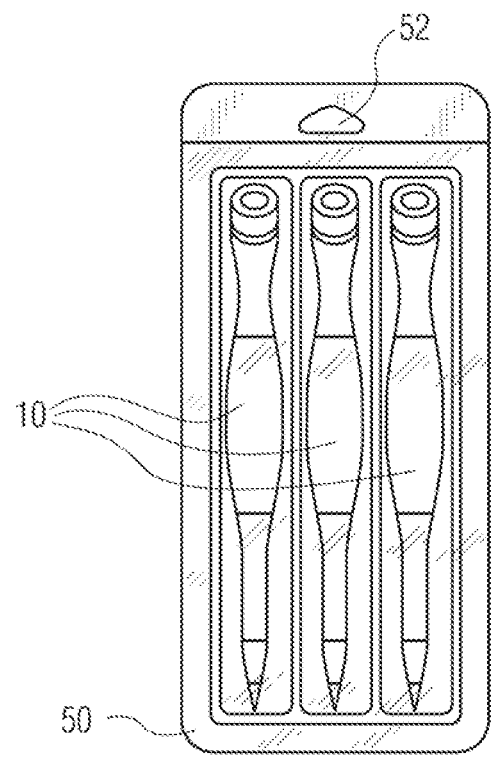
FIGS. 12-13 are front elevational views showing various forms of toothbrushes in a packaged or display condition.
Figure 13:
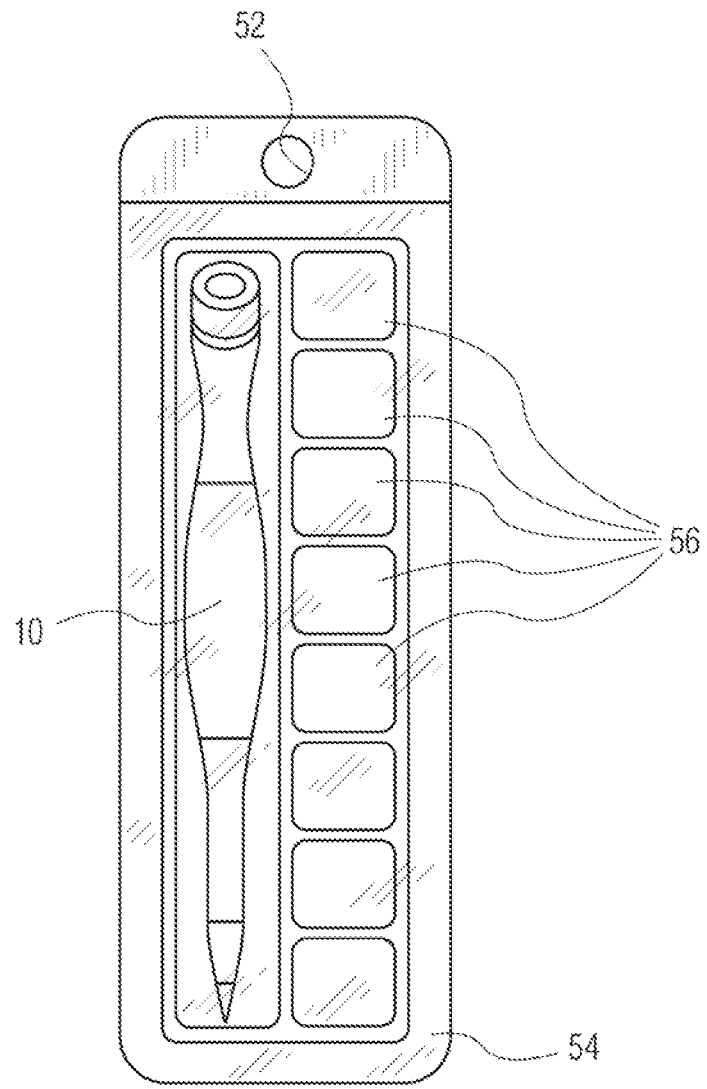

FIGS. 12-13 show different manners of packaging toothbrushes in accordance with this invention. As shown in FIG. 12, for example, a single package 50 could contain a plurality of toothbrushes 10 all of which could be the same or could differ from each other. The package 50 could be of any conventional construction, such as a blister pack, which might include a hole 52 to permit the package to be hung for display purposes.

FIG. 13 illustrates a variation wherein the package 54 includes one or more toothbrushes 10 and a plurality of other components 56 which could be accessories or dispensers or other components. The components could include a small vial of mouthwash. Preferably, the package 50 or 54 would be hermetically sealed to assure freshness. Such hermetic sealing is particularly desired to prevent moisture from reaching gel capsule 32 and causing the capsule to burst.

As is apparent the features herein provide an oral care toothbrush that may be small in size and portable and can be conveniently used away from home under circumstances, such as travel, where water is not readily available.

The features herein could be practiced with a combination of various components that do not involve "toothbrush" usage. In that sense these features may be used in any oral care device or the like, rather than strictly being a toothbrush. Where used as a toothbrush or the like, the features herein may have the advantages, because of the size and configuration, to allow discreet hygienic use, such as no fingers in the mouth, adapting it to be readily used in public areas.

Figure 17:
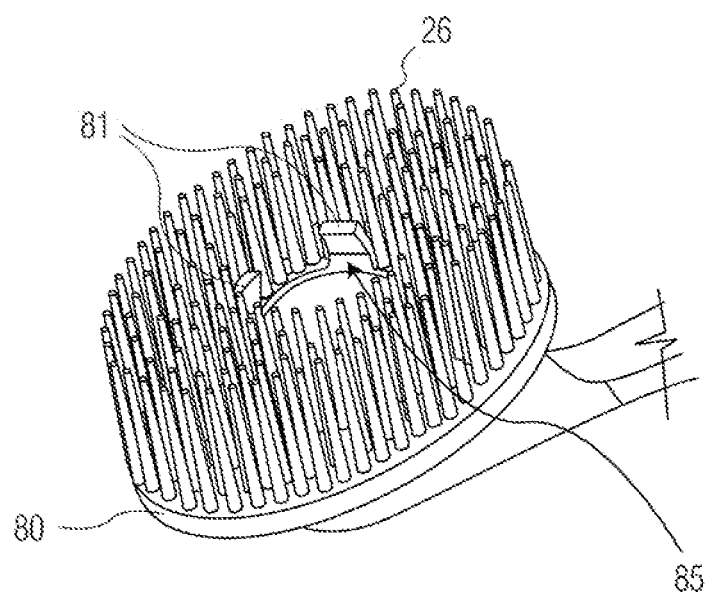
FIG. 17 is a perspective view of an alternate toothbrush head embodiment.

FIG. 17 illustrates another variation in which the head or carrier 80 may have an oval shape, and which may have a series of retaining members 81, such as prongs or biasing members, to hold an oral care dispenser, such as a bead of packed dentifrice or capsule (not shown in the figure), in place prior to use. The retaining members 81 may help retain the bead or capsule at a higher elevation with respect to the field of oral care elements (e.g., bristles 26), to expose more surface area of the bead, dispenser or capsule 32 to the user's saliva to improve the "mouth-feel" and expedite the dissolving of the bead, dispenser or capsule. As illustrated, the retaining members 81 may retain the bead, dispenser or capsule beneath the distal ends of the bristles 26, so as to keep the bead, dispenser or capsule submerged within the field of bristles 26, such that the bristles extend beyond the bead, dispenser or capsule at the bristles' distal ends.

The retaining members 81 may be made of the same material as the bristles 26, or alternatively they may be made of a different material having greater rigidity than the bristles 26. In one construction, the retaining members 81 may be made of the same material as elastomer portions 18.

Figure 18:
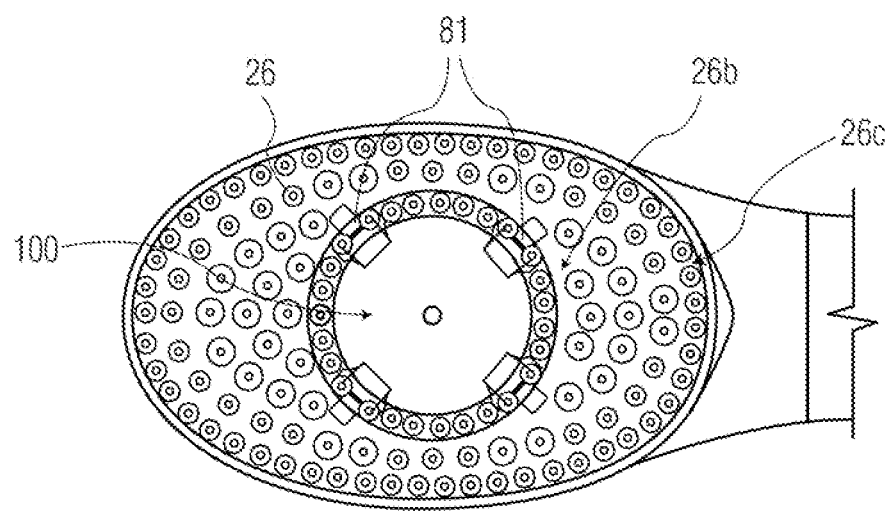
FIG. 18 is an enlarged perspective front view of the head of FIG. 17.

The number of retaining members 81 used may vary depending on the type of bead or capsule, and the amount of retention force assistance. As illustrated in FIG. 18, four retaining members 81 may be used at four cardinal points around the perimeter of the bead or capsule. Greater or fewer retaining members 81 may be used. For example, some embodiments might use three retaining members 81 at triangular points around the perimeter, while other embodiments might use five, six, or more prongs around the perimeter. The retaining members 81 may be positioned such that the bead or capsule is held in a centered position with respect to the bristles 26.

As also shown in FIG. 18, the bristles 26 may vary in diameter at their proximate ends, so that bristles in different areas of the field have different thicknesses and rigidity or axial stiffness as measured from the longitudinal axis of the bristle. In such a construction, inner or central region bristles 26b are stiffer than the outer or peripheral region bristles 26c. The bristles 26 of the carrier 80 may taper towards their distal ends, as seen in FIG. 17.

With reference to FIG. 18, the variable stiffness arrangement of the field of bristles 26 forms a structure for incremental radial flow control of oral care solution/material during a brushing operation for efficient cleaning. This feature is particularly useful for low viscosity oral care solutions released from the dispenser 32. Nevertheless, oral care solutions of higher viscosity can be used in the carrier 80. The bristles surrounding retaining members 81 are independently flexible. In this regard, during a brushing operation, the free ends (e.g., tip) of the stiffer bristles 26b bend relative to their, respective vertical axis less than the outer bristles 26c (e.g., bristles near the periphery). Hence, a portion of the dentifrice stays longer in the central region of the brush head by reduced dynamic bending or action of the stiffer bristles. The sweeping or oscillating motion of the carrier 80 transfers a portion of the retained liquid to the outer region of the carrier 80. While the outer bristles 26c are less stiff, the dynamic bending relative to their vertical axis additionally causes the outer bristles to receive a portion of the dentifrice from the central region of the carrier 80. In this construction, effective cleaning of the tissue surfaces in the mouth may be obtained though the combined use of the variable stiffness bristle field mechanically scrubbing the tissue surfaces and the beneficial effects of applying the oral care material from the dispenser in the oral cavity. In this way, the bristles field provides a limited and controlled flow of the dentifrice or other oral care material to the outer bristles and maintains sufficient flexibility to provide greater user comfort and improved cleaning of the oral tissues.

Figure 19:
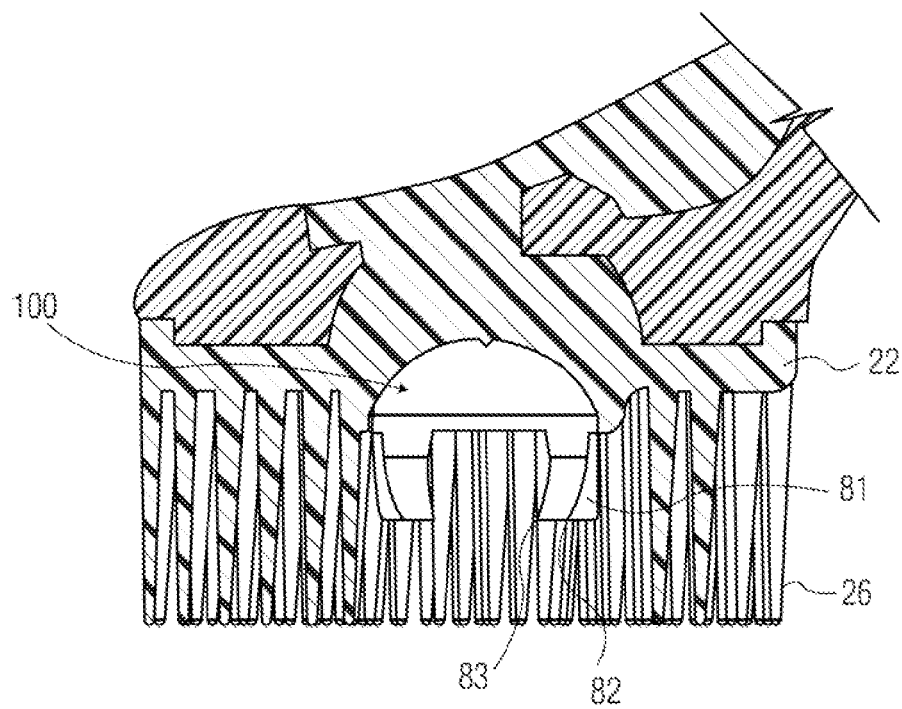
FIG. 19 is an enlarged cross-sectional side view of the head of FIG. 17.

With reference to FIGS. 17-20, in one construction, a basin, or cavity 100 is provided in carrier 80 below the dispenser 32. As can as seen in FIGS. 18 and 19, basin 100 can be a concaved structure or hemispherical structure disposed in the interior area, beneath and between the retaining members 81. While a concaved structure is shown, other shapes for the basin 100 are possible, such as a triangular prism, a square prism or a rectangular prism. The basin 100 serves to retain a portion of the oral care material from the dispenser 32 to extend the beneficial cleaning effects of the oral care material during brushing. In this regard, the sweeping or oscillating motion of the carrier 80 transfers a portion of the retained liquid to inner region bristles 26b of the carrier 80.

In one construction, the retaining members 81 are columnar-like structures that extend upwardly from the carrier 80. The retaining members 81 may curve inwardly to further assist in holding the bead or capsule in place. FIG. 19 illustrates a close-up cross-sectional view, showing such curved retaining members 81. Such curved retaining members 81 may have a length that extends more than halfway up (or down, depending on angle of view) the diameter of the bead or capsule 32 for retention. Hence, a length portion of the retaining members may be acutely disposed with respect to a vertical axis of the carrier 80 for retention. The combination of retaining members 81 provides a compressive force to hold the dispenser 32 in place. The inwardly disposed engaging surface 85 is generally smooth to reliably resist prematurely rupturing the dispenser 32 before use. (See FIG. 17) Also, the smooth and curved characteristic of engaging surface 85 provides for a generally uniform distribution of pressure on the surface of the dispenser 32. This construction thus reduces thin wall stress on the surface of the dispenser 32 to reliably resist prematurely rupturing the dispenser 32 before use. For example, shock forces acting on the toothbrush can be dissipated during transport operations.

The retaining members 81 may assist in rupturing the bead or capsule during brushing, and may have a flat surface at a distal end 82 to form a corner edge 83 against the bead or capsule for this purpose. With reference to FIGS. 17 and 19, some of the bristles 26 may extend from the retaining members 81. In this construction, a portion of the base of the bristle extends from a rear/back of the retaining member 81. This provides a compact space-saving head structure and also provides flow control benefits of the oral care material in the bristle field.

As illustrated in FIG. 19, the block 22 may be made of the same material as some or all of the bristles 26, as discussed above, which may be a different material from other portions of the handle. Alternatively, the handle and block may be made of the same material, with the bristles 26 being made of a different material.

Figure 20:
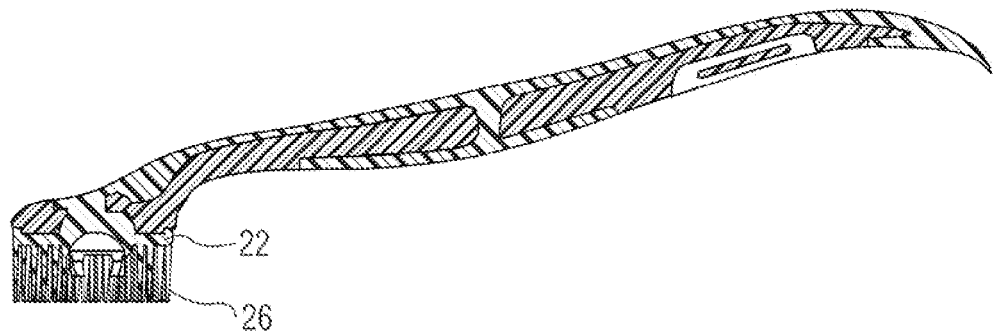
FIG. 20 is a cross-sectional side view of an alternate embodiment toothbrush having the head shown in FIG. 17.

FIG. 20 illustrates a cross-sectional view of a toothbrush having the head or carrier structure shown in FIGS. 17-19. The carrier 80 may be angled at a 10° angle with respect to the handle, representing a less-angled head than that shown in previous figures. An angle ranging from 8° to 12° may assist in improving a user's brushing technique. As with FIG. 19, FIG. 20 also shows an example arrangement of materials, where the block 22 may be made of the same materials as some or all of the bristles 26 and portions of the handle. Alternatively, the handle may be made of the same material as the block 22 and/or bristles 26.

Hence, in some embodiments, an oral care implement may include a rupturable dispenser with a dentifrice, as a connected unit or the various other combinations of components and materials as described. A toothbrush may have a toothpick which enables cleaning between the teeth. A dispenser containing a dentifrice or other oral care material can be connected in the bristle or cleaning element portion of the toothbrush for dispensing the dentifrice to the teeth to provide teeth cleaning and breath freshening or other oral care benefits to a user. In one construction, the oral care elements are configured to slow a radial flow of the oral care material released from the dispenser near an interior region of the carrier and increase a radial flow of the oral care material away from the interior region.

The inventors have also determined that the flavor release time is correlated with the percentage of the total capsule weight provided by the shell of capsule 32. In general, a flavor release time of five seconds or less was achieved with a gelatin shell that provided about 12 wt-% or less of the total weight of capsule 32. Capsules 32 in which the shell formed a higher weight percentage than about 12 wt-% have thicker shells which generally did not dissolve as quickly. In some embodiments, capsules 32 have between about 7 wt-% and about 12 wt-% shell weight, and more preferably between about 9 wt-% and about 12 wt-% shell weight. In some embodiments, capsules 32 having between about 9 wt-% and about 10 wt-% shell weight that provide the desired flavor release time of less than 5.0 seconds are most preferred. Capsules 32 having suitable shells for this purpose may be purchased from Mane, Inc. of Milford, Ohio, or Morishita Jintan Co., Ltd, of Hirakata, Osaka, JP. The capsule 32 preferably has a bead shape having an outer diameter between 3-7 mm, more preferably between 4-6 mm, and most preferably about 5 mm.

As discussed above, in some embodiments, the release time of the oral care dispenser 32, when in the form of a capsule can be controlled by adjusting the properties of the water-soluble shell that contains the oral care material. The invention, however, is not so limited. In other embodiments, any type of water-soluble or degradable barrier can be used to effectuate the desired release time. For example, if the oral care material were included in the tooth cleaning elements, a coating of a water soluble (or otherwise degradable) material can be used to cover the already coated cleaning elements. The solubility rate and/or thickness of the barrier coating can be selected to achieve the desired release time.

Although in some embodiments a desired flavor release time is achieved by controlling the solubility and/or global thickness of the shell of capsule 32 (or other water-soluble or degradable barrier), in other embodiments, the shell of capsule 32 is configured to facilitate a reduced flavor release time.

Figure 24:
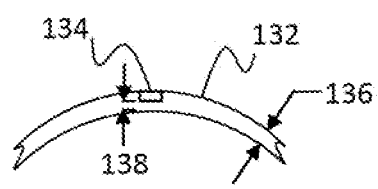
FIG. 24 is an enlarged detail of a portion of the shell of a capsule, modified to include a site with reduced wall thickness.

In some embodiments, the shell of capsule 32 has at least one site where a wall of the shell is relatively weak, such that the shell is configured to release the oral care material from the one site before the oral care material is released at a thicker portion of the shell. For example, in some embodiments, the shell has one or more sites at which the local shell thickness is reduced by a laser treatment. The laser may form one or more discrete, generally cylindrical wells in the capsule wall. FIG. 24 shows an example of a capsule 132 having a cylindrical well 134, at the bottom of which the wall of capsule 132 has a thickness 138 that is thinner than the thickness 136 of the wall in the remainder of the capsule wall. The shell is configured to release the oral care material from the one or more sites before the oral care material is released at a thicker portion of the shell. The number and area of the sites having thinner walls can be selected to control the release rate of the oral care material, and thus the flavor release time.

In some embodiments, the laser may form a "moat" or channel in the surface of the shell, where the channel is in the form of a closed curve, such as a circle or ellipse in a plane offset from the center of the capsule (similar to one of the parallels of latitude encircling a globe). The reduced thickness capsule wall beneath the channel dissolves more quickly than the remainder of the capsule, so that a large section of the capsule shell opens at once, releasing a large amount of the oral care material quickly. In some embodiments, instead of a continuous channel encircling the capsule, the laser may form a plurality of line segments of reduced thickness, where the line segments lie along a circular path encircling the capsule. This structure may provide greater mechanical integrity during handling (compared to a continuous channel), and somewhat slower release of the large section of the capsule shell, so the oral care material is released at an intermediate rate.

Alternatively, the laser may be applied in a tangential direction to thin the wall over a relatively large area of the capsule 32.

In some embodiments, the shell may be partially punctured by inserting a pin part way through the shell, to provide one or more sites at which the local shell thickness is reduced.

Although the shell can be configured to provide rapid release of the oral care material by configuring the shell for dissolving more rapidly at selected sites or portions of the shell, the shell may alternatively be configured to rupture upon application of a pressure. In some embodiments, the shell has at least one region that is configured to rupture upon application of a lower pressure than a remainder of the shell. This function can be achieved by any alteration of the capsule shell to produce a mechanically weak region that is more prone to rupture. Also, some mechanisms have both effects: reducing dissolution time at selected regions of the capsule 32, and at the same time rendering the capsule wall weaker in the same regions, so that the wall ruptures at the selected sites first when subjected to pressure. For example, removal of some of the capsule material at selected sites using a laser can also render those sites more susceptible to rupturing under the pressure applied during brushing.

In some embodiments featuring a rapid-release capsule 32, the head 12 has a plurality of members shaped to retain the oral care dispenser 32 at or near a center of the head, similar to retaining members 81 discussed above with reference to FIG. 17. The plurality of members has smooth surfaces facing the oral care dispenser 32.

Although embodiments providing flavor release time of five seconds or less are described above with reference to oral care implements having bristles 26, in other embodiments, the cleaning element comprises a mass of foam, plastic wool or cotton, such as the mass 34 or 36 described above with reference to FIGS. 5 and 6. In some embodiments, an oral care dispenser 32 in the form of a quick release capsule having a flavor release time of five seconds or less is used in an oral care implement having a mass of foam, plastic wool or cotton 34 or 36. In other embodiments, the mass of foam, plastic wool or cotton 34 or 36 includes an oral care material, such that a flavor release time of five seconds or less is achieved.

In the embodiments described above, a method of achieving a target flavor release time by controlling capsule configuration is described. In other embodiments, a desired flavor release time may be achieved by using one or more alternative techniques, either alone or in combination with each other, or in combination with a capsule-type oral care dispenser 32. For example in an embodiment having a rapid-release capsule 32 as described above, the flavor release time may be enhanced by coating the capsule with a flavored material. The flavored coating may be the same as, or different from, the oral care material inside the capsule 32. The flavored coating material may be an oral care material, or a flavoring without separate medicinal function.

In some embodiments, the oral care dispenser comprises the oral care material in a tablet form. The tablet can be located on the head 12 where the capsule 32 is shown in FIGS. 1-4. The use of the tablet form provides flexibility in the choice of the oral care material, and may add functions. For example, the tablet may include a foaming agent to cause foaming when mixed with saliva, to help disperse the oral care ingredient throughout the user's mouth. Examples of suitable foaming agents include sodium lauryl sulfate, sodium alkyl sulfoacetate, sulfocolaurate, sodium lauroyl sarcosinate, and dioctyl sodium sulfosuccinate. One preferred shape for a tablet (or a capsule) may be an oblong shape, similar to the shape of over the counter two part gelatine capsules. The long thin shape of an oblong can provide the same amount of oral care material in a smaller transverse diameter dispenser, resulting in more bristles on the brush head. An increased amount of bristles may be desirable to provide a more traditional brush-like feel. Furthermore, in embodiments where the dispenser is a capsule, it may be preferable to use a two-part capsule which could provide such benefits such as more precise wall thickness control, and perhaps less interactivity between capsule ingredients during the forming process In other embodiments, the at least one cleaning element comprises a plurality of bristles, and the bristles may act as the oral care dispenser. In some embodiments, the oral care dispenser comprises a coating of oral care material on at least some of the plurality of bristles. By placing at least some of the oral care material on the bristles, a rapid flavor release time can be achieved. In some embodiments, all of the oral care material is provided by the coating on the bristles. In other embodiments, additional oral care material (of the same type as the coating or of a different type) is included in the bristles, which may leak out gradually for extended time-release of the oral care material.

In other embodiments, an oral care material is includes on the bristles for gradual time-release, and a non-medicinal, flavored coating is applied to the surface of the bristles to achieve a desired flavor release time before release of the oral care material. In other embodiments, a flavored coating is applied to the bristles to achieve a desired flavor release time, and the oral care material is provided by a capsule, as described above.

In alternative embodiments, an oral care material having a first flavor is included in the bristles, and the bristles are coated with a coating having a second flavor different from the first flavor (e.g., mint and cinnamon). After an initial burst of the first flavor, the user gradually perceives the second flavor.

Figure 21:
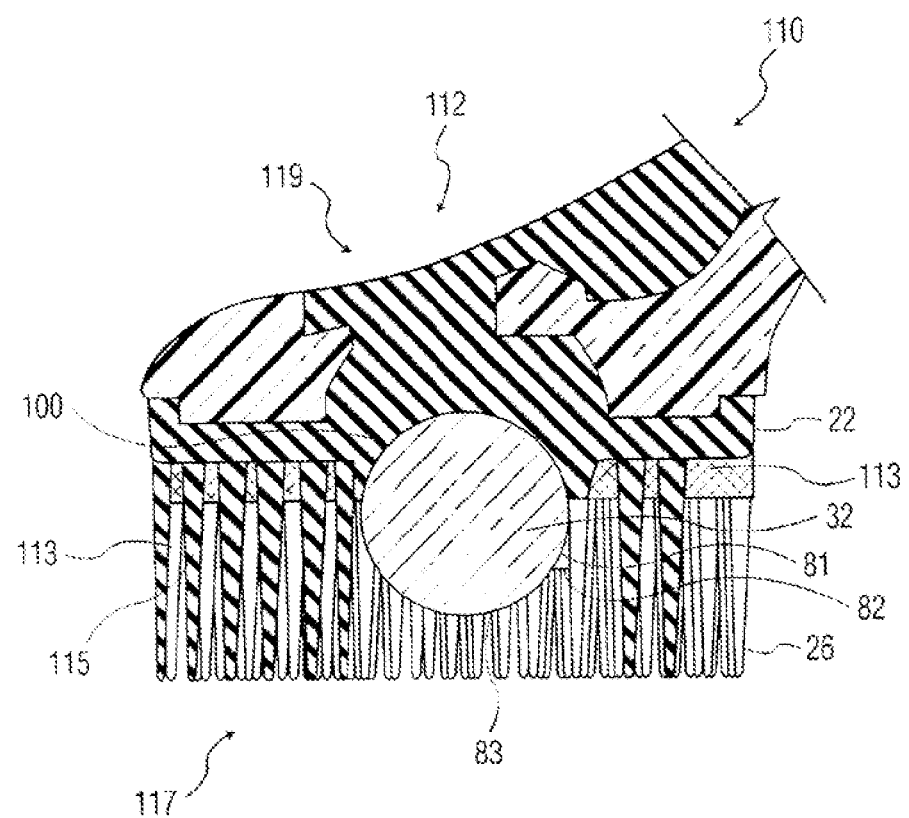
FIG. 21 is an enlarged cross-sectional side view of a head having a film matrix.
Figure 22:
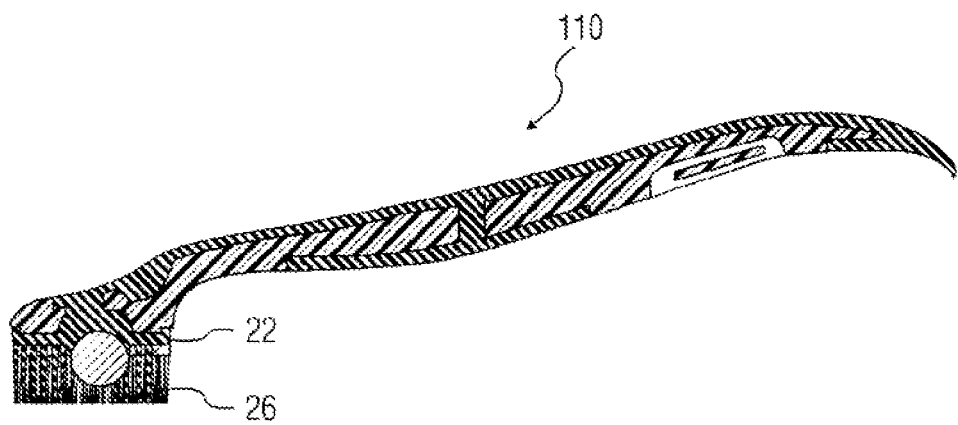
FIG. 22 is a cross-sectional side view of an alternate embodiment toothbrush having the head shown in FIG. 21.

In some embodiments, the oral care dispenser comprises a film matrix retained at the head 12. The film matrix may be a rapid-release version of any of the film matrixes described in U.S. Patent Application Publication No. 2009/0320226A1, Dec. 31, 2009, which is assigned to the Colgate-Palmolive Co., the assignee of the present application. Preferably, the film matrix has a flavor release time of five seconds or less. FIGS. 21-22 illustrate a configuration of an oral care implement in the form of a toothbrush 110 having a head 112 with a first face 117 and an opposite second face 119, which is generally the same as the toothbrush configuration of FIGS. 17-20, except as pertaining to film matrix 113. Film matrix 113 can be a relatively thin film containing one or more agents that can be rapidly released during use of the toothbrush, preferably within five seconds. For example, film matrix 113 can be a starch, polymeric, gelatinous or other type of film configured to retain at least one agent 115 in a stable form and to rapidly release the at least one agent within about five seconds when it comes into contact with saliva and/or is mechanically agitated during use of the toothbrush. Preferably, agent 115 includes a flavor agent, such as a breath freshener or flavorant, that is readily detectable by the user to provide a pleasing burst of flavor upon initial use of the toothbrush 110.

In one configuration, film matrix 113 can be a film matrix as described in U.S. Pat. No. 6,669,929, either with or without the inclusion of film flakes in the film matrix as described therein. Film matrix 113 can be formed from a matrix of hydroxyalkyl methylcellulose starch and starch film forming agents in which is entrained at least one agent 115, such as a colorant (e.g., a dye or pigment), flavorant, sweetener, breath freshener and/or therapeutic agent, such as an antibacterial agent. The film matrix 113 can further include water, additional film forming agents, plasticizing agents, surfactants and emulsifying agents.

Film matrix 113 can be rupturable and/or dissolvable during use in the oral cavity so that flavors, sweeteners, therapeutic agents etc. entrained therein can be maintained substantially separate from dentifrice ingredients during manufacture and storage, such as dentifrice retained in store of dentifrice 132 or dentifrice applied to the toothbrush by the user. Agent 115 within film matrix 113 can be released when the film matrix comes into contact with saliva and/or via the mechanical agitation created during tooth brushing effecting rupture of the film matrix 113 and release of the agent 115.

Film matrix 113 can be prepared by dissolving an hydroxyalkyl cellulose, a starch ingredient, an agent 115, and other film forming ingredients in a compatible solvent to form a film forming composition (not shown). For the configuration of toothbrush 110, the film forming composition is preferably cast onto face first face 117 of head 112 and intermingled with tooth cleaning elements 26. For other configurations, the film forming composition can be sprayed directly on a portion of the toothbrush, such as on the tooth cleaning elements 26.

In some embodiments, the film matrix 113 is in the form of a plurality of flakes or particles on the head 12. For example, in some embodiments, the at least one cleaning element 26 comprises a plurality of bristles, and the oral care dispenser comprises a plurality of flakes on the bristles. The film forming composition can be cast on a releasable carrier (not shown) and dried to form a sheet of film matrix material, which can be cut or otherwise processed to form film matrix flakes or glitter that can be applied to various portions of the toothbrush, such as the tooth cleaning elements and/or soft tissue cleaning elements, as shown in FIG. 23.

Figure 23:
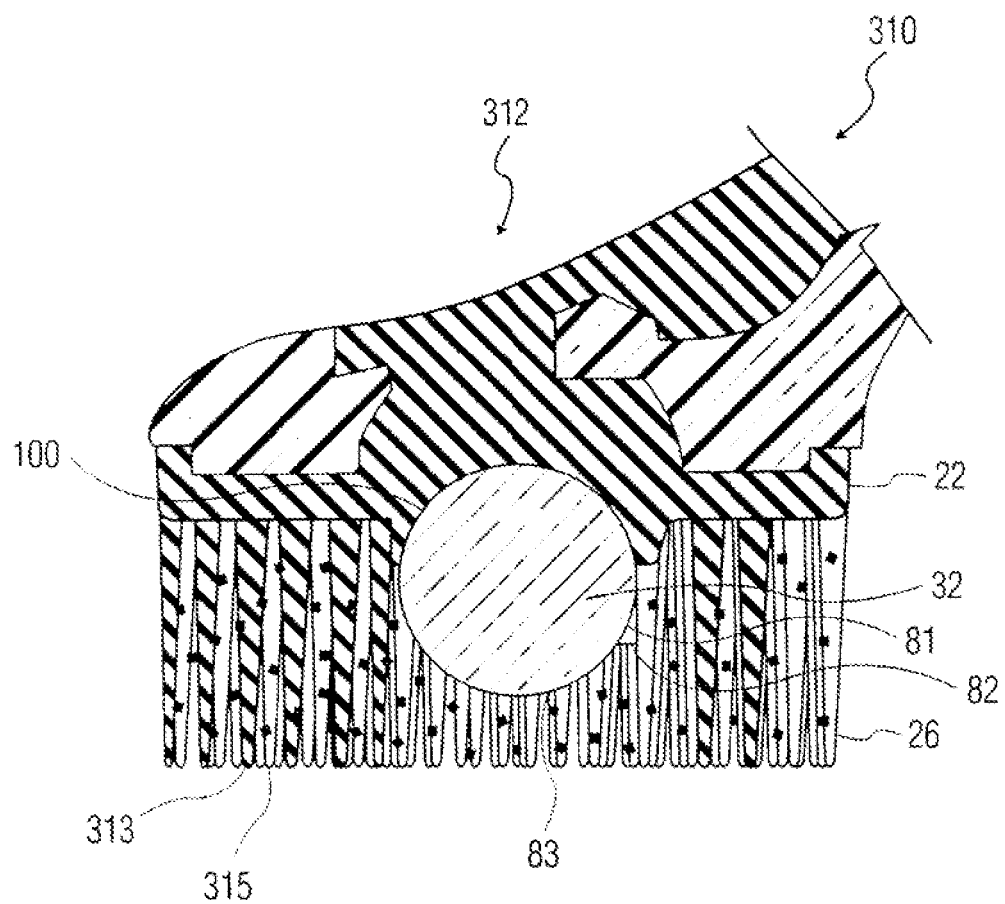
FIG. 23 is an enlarged cross-sectional side view of a head having film matrix flakes.

FIG. 23 illustrates a configuration of an oral care implement in the form of a toothbrush 310 having a head 312 that is similar to the toothbrush configuration of FIGS. 21-22, except as pertaining to film glitter or film flakes 313. Film flakes 313 are a particle or flake form of a film matrix, like film matrix 113, except that it is in the form of pieces or particles of a film matrix that are attached to portions of tooth cleaning elements 26 or other portions of the toothbrush, and provide a flavor release time of about five seconds or less.

Film flakes 313 can be formed via casting a film forming composition on a releasable carrier or mold (not shown) and dried to form a sheet of film matrix material. The carrier material preferably has a surface tension that allows the film solution to spread evenly across the intended carrier width without soaking to form a destructive bond with the film carrier substrates. Examples of suitable carrier materials can include glass, stainless steel, Teflon and polyethylene-impregnated paper. Drying of the film may be carried out at high temperature using a drying oven, drying terminal, vacuum drier, or any other suitable drying equipment that does not adversely affect the ingredients of which the film is composed.

The dried film matrix can subsequently be cut, punched, shredded or otherwise processed into shaped particles, flakes or glitter having a particle size of 0.005 to 0.125 inches and preferably 0.01 to 0.05 inches. Additional stability can be provided to the formed shapes by applying to the film, before shaping into flakes, a protective barrier overcoat such as a food grade shellac or ethyl cellulose. When the film flakes 313 are to be used for decorative effect, the dried film matrix can be formed into various attractively shaped flakes such as hearts, stars, diamonds and circles. Film matrix flakes 313 can include colorants to provide an aesthetically pleasing appearance, such as a glitter appearance.

Film flakes 313 can be applied to various portions of the toothbrush, such as the tooth cleaning elements and/or soft tissue cleaning elements. Film flakes 313 can be applied to tooth cleaning elements 26 while they are wet via spraying or dusting the flakes 313 onto the tooth cleaning elements 26. The film flakes 313 can also be applied via dipping the wet tooth cleaning elements 26 into a stock of film flakes 313. The film flakes 313 can adhere to the tooth cleaning elements 26 via partial dissolution of the film matrix in the water droplets thereon and remain attached to the tooth cleaning elements when dried. Alternatively, the film flakes 313 can be attached via a food grade adhesive.

EXPERIMENT

Figure 25:
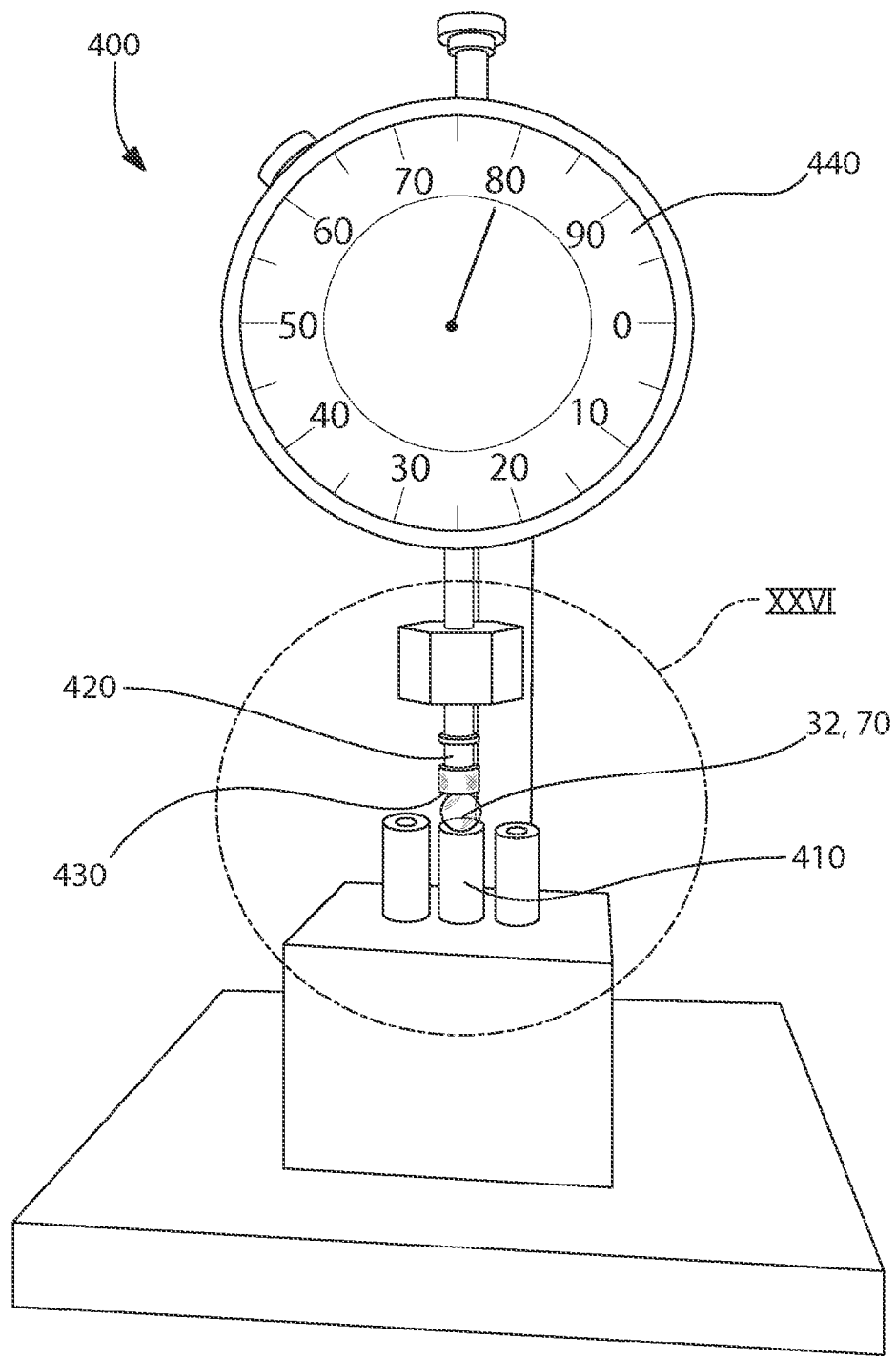
FIG. 25 is a schematic illustration of a dry bead dispense positioned in an experimental apparatus and subjected to a pressure force.
Figure 26:
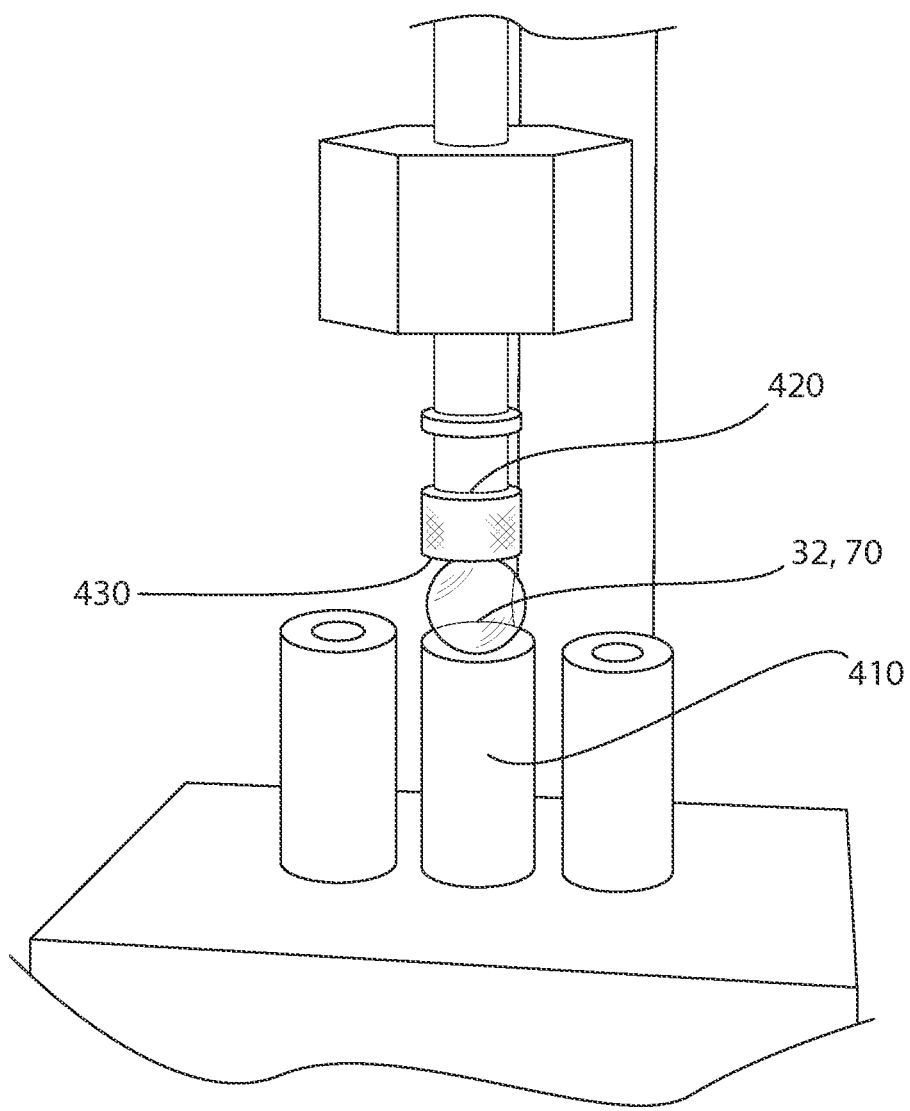
FIG. 26 is an enlarged view of the experimental apparatus of FIG. 25 and the bead being subjected to the pressure force.

With reference to FIGS. 25-26, an experimental apparatus 400 and procedure is depicted in which the release time of the oral care material from a bead dispenser is identified according to one embodiment of the present invention. Referring first to FIG. 25, a gel capsule bead 32, 70 having an approximate 5 mm diameter is positioned atop a cylindrical base 410. The gel capsule bead 32, 70 comprises a water soluble shell comprising porcine gelatin, sorbitol, glycerin and a colorant. Within the gel capsule bead 32, 70 is an oil-based oral care material comprising a medium chain triglyceride (a.k.a. vegetable oil), a flavoring agent, a cooling agent/flavor, and a sucralose solution (containing ethanol and sucralose). Of course, other hydrophobic oral care materials may be desirable so as to not degrade the water-soluble shell.

The cylindrical base 410 is a tubular element having an internal diameter of about 3 mm and a chamfered inside edge.

The experimental apparatus 400 also includes a spring-loaded plunger 420 that is positioned in contact with the top of the bead 32, 70 so that the bead 32, 70 is captured between a flat bottom surface 430 of the plunger 420 and the cylindrical base 410. The experimental apparatus 400 further includes a pressure gauge 440 for measuring the pressure force exerted by the plunger 420. The spring-load of the plunger 420 is adjusted to apply a pressure force equal to a weight of about 80 grams to the bead, which is approximately equal to about 0.78 Newtons. The bead 32, 70 has a shell weight (or thickness) that does not rupture or break when subjected to the aforementioned pressure force. Such toughness is useful in ensuring that the bead 32, 70 can withstand the forces experienced during handling during manufacture and assembly of the bead 32, 70 to the toothbrush head.

Once the bead 32, 70 is in position between the properly calibrated spring-loaded plunger 420 and the cylindrical base 410 (as shown in FIG. 26), the entire apparatus 400 (with the bead 32, 70 in place) is submerged within a water bath (not shown) having a temperature that is about 37.5° C. and a timer is started (not shown). This is illustrated in FIG. 25. Naturally, the water-soluble shell begins to degrade when exposed to the water bath. In certain embodiments, the water bath is an Ultrasonic Cleaner bearing model number TPC-25 made by Telsonic AG.

After a certain period of time passes, the water-soluble shell of the bead 32, 70 will become adequately degraded that the pressure force exerted by the spring-loaded plunger 420 will cause the shell to collapse or partially rupture, thereby releasing the oral care material disposed within the bead 32, 70. The time at which the bead 32, 70 collapses or partially ruptures can be identified by either watching for movement of the plunger 420 or a sharp change in the pressure gauge 440 that is operably coupled to the spring loaded plunger 420. The time it takes from immersion of the bead 32, 70 in the water bath to the release of the oral care material from shell is (or can be equated) to the release time. The inventors of the present application have discovered that the time period between immersion of the bead 32, 70 in the water bath to the release of the oral care material from shell can be adjusted by increasing or decreasing the weight percentage of the shell to the bead. The weight percentage of the shell can also be equated to the thickness of the shell and vice versa.

The inventors of the present invention have used the aforementioned testing procedure and apparatus to create a bead that balances the competing concerns of sufficiently quick release time during water/saliva exposure and shell strength to withstand forces experienced during dry handling in the manufacturing process. In one embodiment, it was discovered that a release time of 5 seconds or less is necessary to create a commercially viable product (as discussed above). While this could be achieved by simply decreasing the shell weight percentage (or shell thickness) to as a small a value as possible, the beads prematurely ruptured during manufacturing handling. Thus, it was determined that for a bead having a 5 mm diameter and composition described above, the bead should preferably have shell that is between 7 wt-% to 12 wt-% of the bead, and most preferably have shell that is between 9 wt-% to 10 wt-% of the bead. Within these ranges, the dry bead exhibited substantial structural integrity during manufacturing and assembly while having a sufficiently fast release time (less than 5 second) when exposed to saliva/water.

Other embodiments will be apparent to those skilled in the art from consideration of the specification disclosed herein. It is intended that the specification and examples be considered as exemplary only, with the true scope and spirit of the invention being indicated by the following claims.

What is claimed is:

1. An oral care implement, comprising:
    a handle; and
    a head connected to one end of the handle,
    wherein the head comprises at least one cleaning element and at least one oral care dispenser, and
    wherein the oral care dispenser is configured to release an oral care material within five seconds when exposed to water having a temperature of about 35° C. to about 40° C.

2. The oral care implement of claim 1, wherein the oral care dispenser includes a water-soluble barrier containing the oral care material.

3. The oral care implement of claim 2, wherein the oral care dispenser is a capsule having a water-soluble shell.

4. The oral care implement of claim 3, wherein the shell is less than or equal to about 12 wt-% of the capsule.

5. The oral care implement of claim 3, wherein the shell is between about 9 wt-% to about 12 wt-% of the capsule.

6. The oral care implement of claim 3, wherein the shell is between about 9 wt-% to about 10 wt-% of the capsule.

7. The oral care implement of claim 3, wherein the capsule is coated with a flavored material.

8. The oral care implement of claim 3, wherein the shell has at least one site where the shell is configured to release the oral care material from the one site before the oral care material is released from another portion of the shell.

9. The oral care implement of claim 3, wherein the capsule has at least one site with a reduced shell thickness, such that the shell is configured to release the oral care material from the one site before the oral care material is released from a thicker portion of the shell.

10. The oral care implement of claim 3, wherein the shell is adapted to rupture upon application of a pressure, and the shell has at least one region that is configured to rupture upon application of a lower pressure as compared to the other regions of the shell.

11. The oral care implement of claim 2, wherein the oral care material is included in the cleaning element, and wherein the water-soluble barrier is a coating on the cleaning element.

12. The oral care implement of claim 2, wherein the oral care material is located on an outer surface of the cleaning element, and wherein the water-soluble barrier is a coating covering the cleaning element and the oral care material.

13. The oral care implement of claim 1, wherein the at least one cleaning, element comprises a plurality of bristles, and at least some of the plurality of bristles include a coating of oral care material on the bristles.

14. The oral care implement of claim 1, wherein the oral care dispenser comprises a hollow chamber within the handle, the hollow chamber containing the oral care material in a liquid form.

15. The oral care implement of claim 1, wherein the oral care dispenser comprises the oral care material in a tablet form.

16. The oral care implement of claim 1, wherein the oral care dispenser comprises a film matrix retained at the head.

17. The oral care implement of claim 16, wherein the film matrix is the form of a plurality of flakes on the head.

18. The oral care implement of claim 1, wherein the at least one cleaning element comprises a plurality of bristles, and the oral care dispenser comprises a plurality of flakes on the bristles.

19. An oral care implement, comprising:
a handle;
a head at one end of the handle; and
a plurality of cleaning bristles attached to the head,
wherein the head comprises at least one oral care dispenser, comprising a water-soluble barrier containing an oral care material,
wherein the barrier is configured to release the oral care material within five seconds when exposed to human saliva.

20. The oral care implement of claim 19, wherein the barrier is between about 9 wt-% of the oral care dispenser and about 10 wt-% of the oral care dispenser.

21. The oral care implement of claim 19, wherein the shell is adapted to rupture upon application of a pressure, and the shell has at least one region that is configured to rupture upon application of a lower pressure as compared to the other regions of the shell.

22. The oral care implement of claim 19, wherein the capsule has at least one site with a reduced shell thickness, such that the shell is configured to release the oral care material from the one site before the oral care material is released from a thicker portion of the shell.

23. The oral care implement of claim 19, wherein the head has a plurality of members shaped to retain the oral care dispenser at or near a center of the head, the plurality of members having smooth surfaces facing the oral care dispenser.

24. The oral care implement of claim 19, wherein at least one of the plurality of cleaning elements include a coating.

25. An oral care implement, comprising:
a handle; and
a head connected to one end of the handle, the head having at least one cleaning element and at least one oral care dispenser,
wherein the at least one oral care dispenser comprises a moisture degradable shell containing an oral care material,
wherein the shell is less than or equal to about 12 wt-% of the oral care dispenser; and
wherein the shell releases the oral care material within five seconds when the shell is either: (1) exposed to water having a temperature of about 35° C. to about 40° C.; or (2) exposed to human saliva.

26. The oral care implement of claim 25 wherein the shell comprises between about 9 wt-% of the oral care dispenser and about 10 wt-% of the oral care dispenser.

27. An oral care implement, comprising:
a handle;
a head connected to one end of the handle, the head having at least one cleaning element; and
a capsule containing an oral care material disposed within the head;
wherein the oral care dispenser is configured to: (1) not release the oral care material when subjected to a predetermined pressure force when dry; and (2) release the oral care material within five seconds when exposed to water having a temperature of about 35° C. to about 40° C. while being subjected to the predetermined pressure force; and
wherein the predetermined pressure force is between 0.68 Newtons and 0.88 Newtons.

28. The oral care implement of claim 27 wherein the predetermined pressure force is about 0.78 Newtons.

29. The oral care implement of claim 27 wherein the capsule comprises a water-soluble shell and the oral care material is hydrophobic.

* * * * *